(12) United States Patent
Darnell et al.

(10) Patent No.: US 6,750,029 B1
(45) Date of Patent: Jun. 15, 2004

(54) METHODS AND AGENTS FOR THE DETECTION AND MODULATION OF CELLULAR IMMUNITY TO IMMUNE PRIVILEGED ANTIGENS

(75) Inventors: Robert B. Darnell, Pelham, NY (US); Matthew L. Albert, New York, NY (US); Nina Bhardwai, Montclair, NJ (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 09/603,635

(22) Filed: Jun. 26, 2000

Related U.S. Application Data

(60) Division of application No. 09/343,151, filed on Jun. 29, 1999, now abandoned, which is a continuation-in-part of application No. 09/107,978, filed on Jun. 30, 1998, now abandoned.

(51) Int. Cl.[7] ............................................. G01N 33/53
(52) U.S. Cl. ..................................................... 435/7.24
(58) Field of Search ........................................ 435/7.24

(56) References Cited

U.S. PATENT DOCUMENTS

| 5,686,068 A | 11/1997 | Melief et al. ............ 424/93.71 |
| 5,753,522 A | 5/1998 | Polans et al. ................ 436/518 |

FOREIGN PATENT DOCUMENTS

| WO | 92/19635 | 11/1992 |
| WO | 93/03375 | 2/1993 |
| WO | 00/00825 | 1/2000 |

OTHER PUBLICATIONS

Albert et al., Nature, (1998), 392: 86.
Altman et al., Science (1996), 274(5284): 94–96.
Banchereau et al., Nature (1998), 392: 245–52.
Boon et al., Curr. Opin. Immunol., (1997), 9: 681.
Cohen et al., Blood, (1997), 89(12): 4636–45.
Corradi et al, J Neurosci, (1997), 17: 1406.
Dalmau et al., Medicine, (1991), 71: 59–72.
Darnell, Proc Natl Acad Sci, (1996), 4529–4536.
D'Orazio et al., J. Immunol., (1998), 160: 2089–98.
Fathallah–Shaykh et al, Proc. Natl Acad Sci USA, (1991), 88: 3451.
Medawar et al., Br. J. Exp. Pathol. (1995), 29: 58–59.
Neumann et al., J Exp Med, (1997), 185: 305–316.
Neumann et al., Science, (1995), 269: 549–552.
Peterson et al., Neurology, (1992), 42: 1931–37.
Posner et al., Curr Opin Immunol (1997), 9: 723.
Saas et al., J. Clin Invest. , (1997), 99: 1173–78.
Sakai et al., Ann Neurol., (1990), 28: 692–98.
Tanaka et al., Clin Neuro Neurosurg. (1995), 97: 97.
White et al., J. Neurosci, (1998), 18: 1428–39.

*Primary Examiner*—David Saunders
(74) *Attorney, Agent, or Firm*—Klauber & Jackson

(57) ABSTRACT

Recognition of the role of a cellular immune response to immune-privileged antigens in the etiology of paraneoplastic syndromes and tumor immunity has provided diagnostic and therapeutic methods for the detection of paraneoplastic antigen-specific cells, enhancing tumor immunity by increasing the population of cytotoxic T lymphocytes (CTLs), and suppressing cellular immunity to treat the paraneoplastic syndrome. Methods for the detection of memory and cytotoxic T lymphocytes are provided which utilize immune-privileged antigens or their peptides. Enhanced CTL production is provided by stimulating antigen presenting cells in vitro with immune-privileged antigen, with and without further exposure to T lymphocytes, prior to reintroduction of either the antigen-presenting cells and/or the T lymphocytes into the patient. Suppression of the cellular response to non-tumor cells expressing the immune-privileged antigen is provided by using agents which suppress; anti-cytokine therapy is also provided to limit cell surface expression of paraneoplastic antigens by non-tumor cells. Compositions comprising immune-privileged antigen peptides useful for diagnostic methods and therapeutic treatments are also described.

24 Claims, 7 Drawing Sheets serum CSF

Activated CTL Response

Recall CTL Response

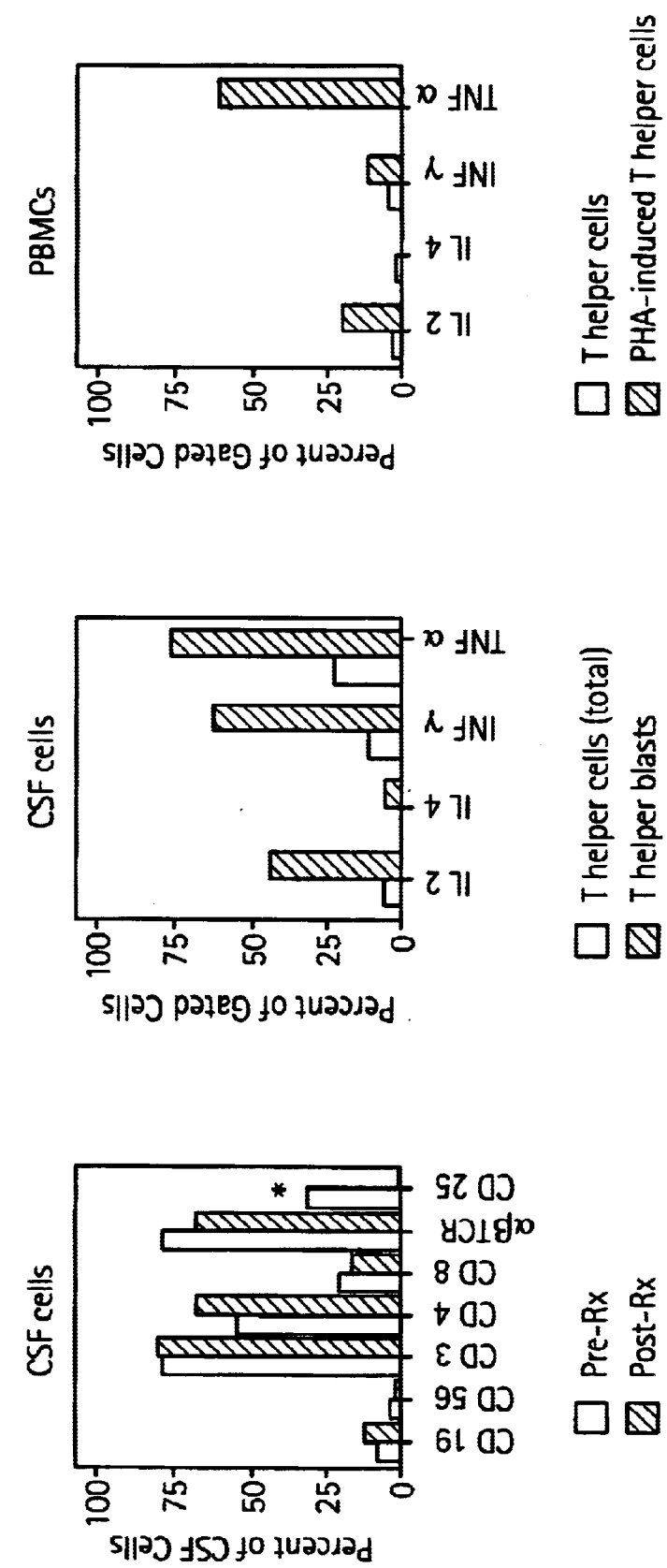

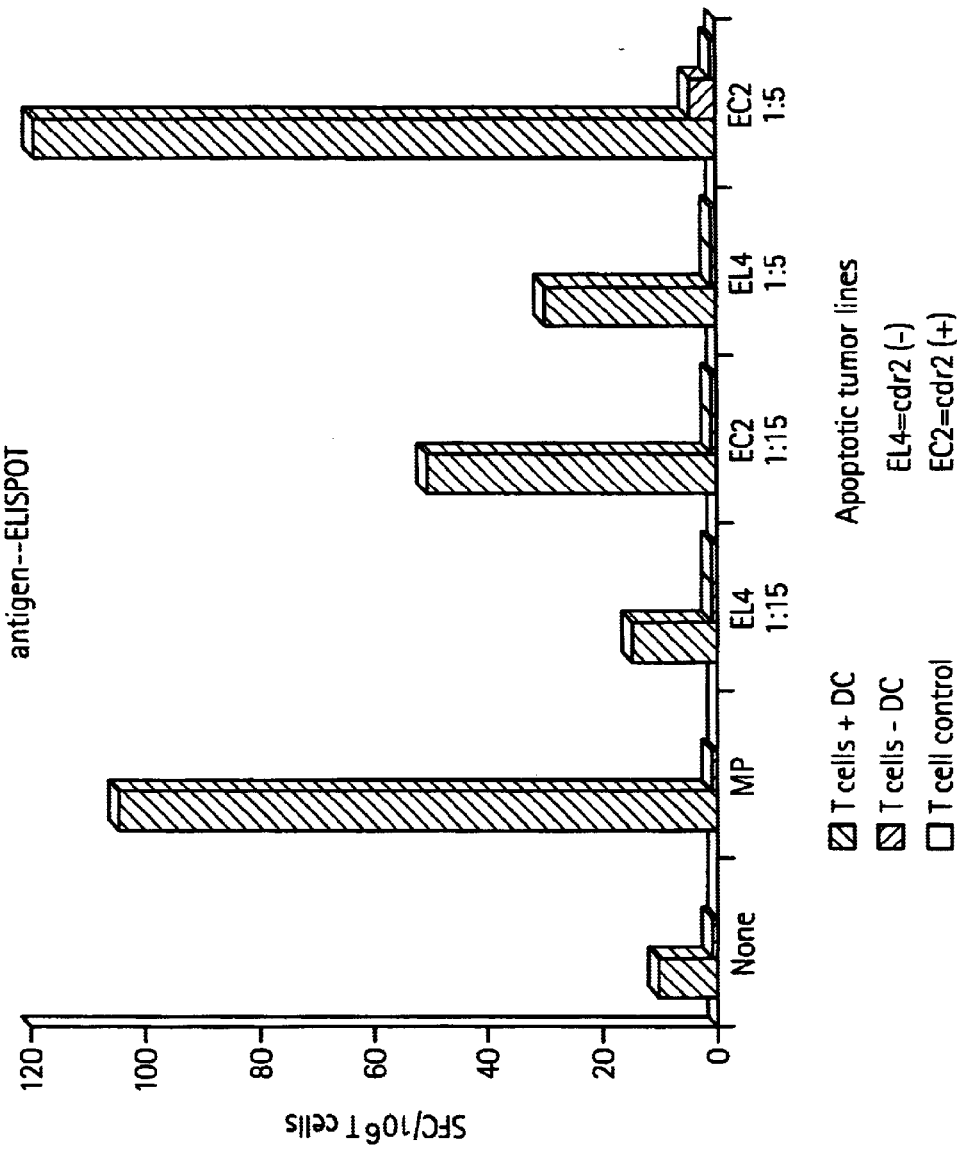

METHODS AND AGENTS FOR THE DETECTION AND MODULATION OF CELLULAR IMMUNITY TO IMMUNE PRIVILEGED ANTIGENS

CROSS-REFERENCE TO RELATED APPLICATION

This application a divisional of Ser. No. 09/343,151, filed Jun. 29, 1999 and now abandoned, which is a Continuation-in-part of Ser. No. 09/107,978, filed Jun. 30, 1998 now abandoned.

GOVERNMENTAL SUPPORT

The research leading to the present invention was supported, at least in part, by grants from the Department of Defense, Breast Cancer Research Award No. DAMD017-94-J-4277, the National Institutes of Health Award No. M01 RR00102, and the National Multiple Sclerosis Society. Accordingly, the Government may have certain rights in the invention.

FIELD OF THE INVENTION

This invention relates to diagnostic and therapeutic methods based upon the development of cellular immunity to immune privileged antigens and its role in the etiology of paraneoplastic neuronal disorders and tumor immunity, among other conditions.

BACKGROUND OF THE INVENTION

Constant surveillance of epitopes throughout those structures in the body accessible to the immune system provides a very effective means for recognizing and maintaining "self" and destroying epitopes and their carriers which invade the body or arise pathologically, such as infectious microorganisms. One important role of immune surveillance is the recognition and destruction of neoplastic cells that are believed to arise continuously in the body and for the most part are eliminated by the immune system before becoming detectable. However, examples of naturally-occurring tumor immunity have been elusive. Cytotoxic T lymphocytes, key participants in effective immune surveillance, are not expanded in patients with active tumors, even when these tumors express what are believed to be tumor-specific antigens such as the MAGE/MART antigens of melanoma.

Effective tumor immunity has been documented, however, in individuals with paraneoplastic neuronal disorders (PNDs). These syndromes are poorly understood diseases in which serious effects of cancer in the body occur in the nervous system without any direct involvement of the tumor. PND patients typically present to physicians with neurologic dysfunction unaware that they harbor a tumor. For example, patients with ovarian or breast cancer who develop paraneoplastic cerebellar degeneration (PCD) have an effective tumor immune response (3,4,5; reviewed in 1,2,6), and moreover, the tumor expresses neuron-specific proteins (antigens). These patients have in circulation and in the cerebrospinal fluid (CSF) antibodies against these tumor cell antigens, which also cross-react with the same proteins expressed in neurons, termed onconeural antigens. A high titer antibody recognizes the intracellular antigen cdr2 expressed in the ovarian or breast tumor present in PCD patients (10); and also recognizes the antigen in Purkinje neurons of the cerebellum (10). However, as will be elaborated below, the existence of this antibody does not account for the etiology of the PND nor for effective tumor killing.

Certain regions of the body, such as the brain, eye, and testis, are protected from immune surveillance, these sites are referred to as immune privileged. Based on the above observations, the immune system is proposed to initiate PCD by recognizing the normally immune-privileged antigen cdr2 (10) when it is ectopically expressed in gynecologic tumors. This immune response is associated clinically with effective tumor immunity, and is believed to lead to the recognition and destruction of Purkinje neurons expressing cdr2. cDNAs encoding several of the target antigens have been cloned, for example, cdr2 which has been shown to be the correct tumor antigen (9,54). However, because the target neuronal antigen is cytoplasmic, the role of circulating and cerebrospinal fluid (CSF) antibodies against these antigens in the pathogenesis of PCD is questionable. Moreover, attempts to reproduce the disorder by passive or active transfer of antibodies have failed (11,12,13). As the target organ, the brain, is immune privileged, and furthermore the target antigen is cytoplasmic, the etiology of the paraneoplastic syndrome is difficult to reconcile. This is further confounded by the apparent absence of a cellular immune response against tumor antigens in general and the apparent absence of a cellular immune response in PCD. No cytotoxic T lymphocytes were found against the cdr2 protein using autologous dendritic cells in a patient with PCD (47). The etiology of tumor immunity in PND is enigmatic.

As described above, the paraneoplastic syndromes are serious conditions associated with tumors and frequently affect the central nervous system; these disorders are collectively referred to as paraneoplastic neuronal disorders (PND). For example, one common paraneoplastic disorder which is seen in patients with breast or ovarian cancer is paraneoplastic cerebellar degeneration, or PCD, in which a progressive and severe neurological dysfunction occurs involving the cerebellum, leading to dyscoordination of the legs and arms, dizziness and double vision. Frequently, these symptoms appear before the diagnosis of cancer. In another example of neurological degeneration, Hu syndrome is associated with small cell lung cancer and antibodies to the onconeural antigen Hu. In other examples, opsoclonus, or spontaneous, chaotic eye movements, and myoclonus, jerky body movements, may accompany breast cancer, fallopian tube cancer, or small cell lung cancer, and are associated with antibodies to the onconeural antigen Nova.

The target onconeural antigens have yet to be identified for some disorders believed to be paraneoplastic. Patients with Hodgkin's disease and other lymphomas may develop subacute cerebellar degeneration that is believed to be immune mediated (22,42). Eaton-Lambert syndrome, a condition causing weakness in the limbs, may also accompany intrathoracic tumors such as lung cancer and is believed to be immune mediated (2). Some patients who develop spinal cord dysfunction (e.g., myelopathy), motor neuron diseases, blindness and other neurologic symptoms are found to have specific sets of underlying tumors and are believed to have immunity to unknown or partially-characterized onconeural antigens (2,37). Less well understood, the incidence of the muscle diseases dermatomyositis and polymyositis is increased in cancer patients. The dermatologic condition vitiligo, in which melanocytes producing skin pigment are destroyed, appears associated with a decrease in incidence of melanoma. It is thus apparent that an association exists between tumors, and in some cases tumor immunity, and the sites of the paraneoplastic disorder symptoms, perhaps through the existence of some common antigens.

Several lines of evidence suggest the existence of naturally-occurring tumor immunity in PND patients. PND-associated tumors are typically occult (24,25); in several cases they have been identified only by microscopic analysis of suspect organs following exploratory surgery or at autopsy. Patients with PND-associated tumors have significantly-limited disease and an improved tumor prognosis relative to patients with histologically-identical tumors unassociated with PND (20,24,26–28). In some cases PND-associated tumors have been documented to regress with the onset of autoimmune neurologic disease (7).

Specific clinical data regarding anti-tumor immunity is available for several of the PNDs. Patients with paraneoplastic encephalomyelitis harbor high titers of an antibody termed Hu and small cell lung cancers (SCLCa); their tumors are typically limited to single nodules (53/55 [96%] patients in the most complete study published [3]). This is a remarkable finding given that most SCLCa patients from unselected series (over 60%) have widely metastatic disease at the time of diagnosis (and no detectable titers of Hu antibody). In addition, fifteen percent of SCLCa patients without PND nonetheless have detectable titers of the Hu antibody (20). These patients have statistically significant increases in the frequency of limited stage disease, complete response to chemotherapy and longer survival (3,5). These results suggest that anti-PND antibodies may be associated with suppression of tumor growth independently from their association with neurologic disease.

There are also firm associations between the presence of the Nova (Ri) (28) and Yo (10) antibodies in PND patients and clinically-limited malignancy. Both antibodies are found in women with gynecologic cancer. Of 52 Yo-antibody-positive patients with breast or ovarian cancer (4), two-thirds (34/52) presented with neurologic symptoms prior to the diagnosis of cancer, and 87% (45/52) had limited oncologic disease when diagnosed; similarly, 4/7 Nova-positive patients presented with neurologic symptoms, 6/7 had limited stage disease, and no tumor could be found in one patient (28). By comparison, only 50–60% of unselected breast cancer patients, and 25% of ovarian cancer present with limited stage disease (8).

Experimental observations support the clinical evidence that there is immunologic recognition of tumor cells in PND. High titer anti-PND antibodies are found in the serum and cerebrospinal fluid of PND patients. In vitro, these antibodies react specifically with tumor specimens obtained from PND patients cells, as well as neurons from clinically affected areas of the nervous system (24,25, 29). For example, 10/10 breast or ovarian tumors from Yo-positive patients were immunoreactive with biotinylated Yo antisera (4), and 3/4 breast or fallopian tumors from Nova-positive patients were immunoreactive with biotinylated Nova antisera (28). Taken together, these observations suggest that PND antibodies are more than markers for neurologic disease or even the presence of tumor cells, but are markers, and perhaps in part reflective of effective anti-tumor immune responses.

The immunologic basis of the anti-tumor and antineuronal immune response in PND is unknown. The finding of autoantibodies with neuronal binding specificity, and observations on autoimmune neurologic disorders of the peripheral nervous system, have focused attention on the role of B cells in the pathogenesis of PND. In myasthenia gravis (MG) and Lambert-Eaton myasthenic syndrome (LEMS), antineuronal antibodies have been found to passively transfer autoimmune disease in animals (30, 31). In PND, there are relatively higher titers of antibody in the CSF than serum (IgG index>1) (32) suggestive of an active B cell inflammatory response within the CNS compartment. Furthermore, although the data is not fully compelling, there have been numerous reports that PND antibodies may be neurotoxic in vitro and that antibodies may be able to be taken up by neurons (33,34). These observations have led clinicians to focus therapy for the PNDs on the elimination of PND antibodies. Unfortunately these attempts have been uniformly unsuccessful (24, 32, 35). Several features of the PNDs distinguish them from MG and LEMS and suggest that B cells might not be sufficient or even necessary for the development of PND. PND antigens have been found to be cytoplasmic (Yo, β-NAP) or nuclear (Nova, Hu) proteins, unlike the target antigens in MG (the acetylcholine receptor) or LEMS (the presynaptic calcium channel) (2). It is difficult to reconcile these observations with the premise that PND antibodies play a primary role in PND autoimmunity. Moreover, attempts to produce animal models of PND, including infusion of antibody into the CSF and immunization with cloned fusion protein, have failed (11, 12).

Thus, the etiology of the paraneoplastic syndromes appears to have an immunological basis, heretofore undefined. It is towards a better understanding of the etiology of the paraneoplastic neuronal disorders and the establishment of a link between effective tumor immunity and these serious, remote complications of neoplasia in immune privileged sites that the present invention is directed, with objectives of improving the detection of tumors and paraneoplastic disorders in individuals in general and offering improved therapies for both tumors expressing immune privileged antigens and the associated syndromes.

SUMMARY OF THE INVENTION

The inventors herein have made the surprising and remarkable finding of the presence of tumor antigen-specific T lymphocytes (CTLs) in patients with paraneoplastic neuronal disorders. This finding provides a basis for understanding the desirable and often effective cell-based immunologic attack on the tumors, and the effective but undesirable attack on remote target organ(s) of the paraneoplastic disorders by CTLs. Expression of the same immune-privileged antigen by these remote tissues as that which is expressed in the tumor cells, and to which T lymphocytes are targeted, explains for the first time the etiology of the PNDs. Both activated CTLs and memory T lymphocytes specific for the tumor and for the remote antigen have been detected. This finding provides an appreciation that immune privileged antigens offer a unique set of targets for the immune system. If expressed in tumors, they provide targets for effective anti-tumor immunity. If immune-privilege or tolerance to these antigens is broken, for example in the setting of effective anti-tumor immunity, autoimmune disease may result. The identification of a cellular immune response to immune-privileged antigens that can be readily and specifically detected, amplified, or inhibited, provides the basis for diagnostic and therapeutic utilities disclosed herein. Based upon this discovery, diagnostic utilities are disclosed for the detection and monitoring of cellular immunity to privileged antigens, and therapeutic methods are described for increasing the effectiveness of anti-tumor immunity and also for protecting the immune privileged site from immune-mediated pathology. Known diagnostic and therapeutic procedures and manipulations of the immune system are modified based on the discoveries herein in order to detect and modulate the immune response to immune-privileged antigens.

As will be described in more detail, below, only a fraction of patients with a specific T lymphocyte response to immune privileged antigens, especially those with tumors, exhibit an overt paraneoplastic disorder, yet such patients are at risk for the development of, or may have as-yet undetected autoimmune disease or another subclinical disorders. In accordance with the present invention, methods for determining in an individual the presence and extent of a cellular immune response to an immune-privileged antigen are provided, the cellular immune response associated directly or indirectly with a pathological state. Examples of pathological states include but are not limited to dysproliferative diseases, paraneoplastic syndromes, and autoimmune disorders. The method comprises quantitating in a sample of bodily fluid from an individual the presence and extent of T lymphocytes specific for the immune-privileged antigen or its fragments. The preferred method involves the detection of T lymphocytes which recognize paraneoplastic antigens, and most preferably, onconeural antigens such as cdr2 and Hu antigen. One example of a means for detection comprises determining the extent of activation of T lymphocytes upon exposure to the antigen by measuring cytokine production; another method comprises detecting the extent of recognition by the cytotoxic T cells of target cells expressing the antigen. Methods for detecting T lymphocytes bearing receptors for immune-privileged antigen are also provided.

In the instance where the T lymphocytes to be detected are memory T cells, the methods comprises detecting the extent of activation of memory T cells after exposure to antigen-presenting cells (APCs) presenting the immune-privileged antigen. In another embodiment, the extent of recognition of target cells expressing the antigen is determined after exposure of the memory T lymphocytes to APCs presenting the immune-privileged antigen.

The present invention further provides a method for screening individuals for the presence of tumors expressing immune-privileged antigens as well as detecting the early onset or propensity to develop a pathological state caused by a cellular immune response to an immune-privileged antigen. This method comprises measuring the presence and extent of T lymphocytes specific for immune privileged antigens. Furthermore, a method is provided for determining whether a neoplasm expresses an immune-privileged antigen by quantitating T lymphocytes that are specific for the antigen or its fragment. In another embodiment, a method is disclosed for determining whether a patient with a immune-privileged antigen-expressing tumor has a sufficient population of antigen-specific T lymphocytes to control the tumor or is a candidate for anti-cancer therapy. This method comprises quantitating T lymphocytes specific for the antigen or a fragment. In a still further embodiment, a method for monitoring the effectiveness of therapies directed to modulate the population of immune-privileged antigen-specific T lymphocytes in a patient is described wherein the numbers of antigen-specific T lymphocytes are quantitated.

The cDNAs encoding the target immune-privileged as well as their expressed proteins and fragments thereof may be used in the present invention to provide reagents for carrying out the diagnostic and therapeutic methods as described herein, as well as being part of a diagnostic kit. As described above, the sequence and cDNA of cdr2 is known (9,54); its fragments that complexes with HLA are described below.

In a further example of a screening method for identifying the number of immune-privileged antigen-specific T cells in a patient sample, the following steps may be carried out:
i) maturing dendritic cells in the blood sample;
ii) exposing the matured dendritic cells to apoptotic debris from unrelated cells expressing an immune-privileged antigen;
iii) co-incubating the immune-privileged antigen-exposed dendritic cells with the peripheral blood lymphocytes from the patient; and
iv) correlating the amount of interferon-γ released from the lymphocytes with the number of immune privileged antigen-specific T cells in the sample.

By way of non-limiting example, the immune-privileged antigen may be cdr2. The unrelated cells expressing an immune-privileged antigen may be cells stably transfected to express an immune-privileged antigen, such as cdr2. The interferon-γ release may be measured in an ELISPOT assay.

Diagnostic kits are also provided with componentry capable of measuring the above-described T lymphocytes and antigens comprising, for example, one or more of the following reagents: an isolated, immune-privileged antigen or preferably a fragment of the immune-privileged antigen; a target cell expressing the immune-privileged antigen or its fragment; a fragment of the immune-privileged antigen in a tetrameric complex with HLA; and a reagent such as an antibody or labeled antibody which recognizes a fragment of the immune-privileged antigen in a complex with HLA. When the immune-privileged antigen is cdr2, useful isolated polypeptide sequences identified include cdr2 peptides referred to as Yo1 through Yo8, or cdr2-1 through cdr2-8, and identified herein as SEQ ID NO:1, SEQ ID NO:2, SEQ ID NO:3, SEQ ID NO:4, SEQ ID NO:5, SEQ ID NO:6, SEQ ID NO:7 and SEQ ID NO:8. The kit may include target cells prepared from a cell line or, for example, Drosophila, which expressed the immune-privileged antigen, and further may express HLA molecules and co-stimulatory molecules. A kit may further include components for detecting cytokine production, such as γ-IFN, as a means for detecting immune cell activation. To broadly screen samples from a variety of patients with different HLA haplotypes, a variety of target cells expressing the same immune-privileged antigen, but different HLA haplotypes, may be employed in order to detect immune-privileged antigen specific T lymphocytes regardless of the patient's HLA haplotype.

It is another object of the present invention to provide methods for treating a neoplasm in a patient in which the neoplasm expresses an immune-privileged antigen. One preferred embodiment is accomplished by increasing the number of immune-privileged, antigen-specific cytotoxic T lymphocytes present in the patient. In one, non-limiting example, the method is carried out by first isolating a quantity of APCs from a sample of the patient's blood, then exposing the APCs in vitro to the immune-privileged antigen or its fragment, followed by reintroducing the antigen-exposed APCs to the patient. In another related embodiment, the same method is followed with an additional step of exposing the antigen-exposed APCs in vitro to a quantity of T lymphocytes isolated from the patient, and reintroducing the T lymphocytes to the patient. These examples are illustrative of methods of providing the patient with immune privileged antigen-specific T lymphocytes and/or immune-privileged antigen-presenting APCs in order to develop or enhance immunity to the tumor.

Methods for achieving presentation of the immune-privileged antigen or its fragment on the APCs in the aforementioned methods is achieved using any one of several methods. For example, APCs are provided with apoptotic cells expressing the immune-privileged antigen or a fragment. These can be commonly available cell lines expressing the immune privileged antigen, such as HeLa cells, which express the cdr2 antigen (9), or transfected cells such as Drosophila cells expressing the gene encoding the immune-privileged antigen. These cells may also be further engineered to additionally express the gene encoding the MHC molecule haplotype of the patient, and even further engineered to express co-stimulatory molecules, such that the Drosophila cells function as an antigen-presenting cell, thus forming a useful APC for in-vivo or ex-vivo stimulation of T lymphocytes as described above. These cells also have diagnostic utility, as described herein. The preferred antigen is a paraneoplastic antigen, and most preferred, an onconeural antigen such as cdr2 and Hu antigen. In a further embodiment, the immune-privileged antigen-specific T lymphocytes are derived from a donor individual of the same HLA haplotype as the patient.

In a further embodiment of the present invention, a method for treating a pathological state in a mammal is provided, wherein the pathological state is caused by the presence in the mammal of T lymphocytes specific for an immune-privileged antigen. The method consists of administration of an effective amount of an agent which decreases the population of activated T lymphocytes specific for cells expressing the immune-privileged antigen. Non-limiting examples of such agents include tacrolimus, cyclosporin, immunosuppressive cytokines, corticosteroids, and combinations. The preferred agent is tacrolimus. The immune-privileged antigen is preferably a paraneoplastic antigen, most preferably, and onconeural antigen such as cdr2 and Hu antigen and their fragments. The preferred route of administration of the agents is to the central nervous system. Other effective routes of administration are also disclosed.

In a further embodiment of the present invention, a method is provided for decreasing the ability of non-tumor cells expressing privileged antigens to be killed by cytotoxic T lymphocytes as well as decreasing the expression of paraneoplastic antigens on non-tumor cells. These may be achieved by several methods, for example, by reducing the cytokine level in contact with the affected cells; increasing the expression of Nef or Nef-like proteins, inhibiting perforin-mediated CTL killing of neurons, and inhibiting apoptosis of the target cells.

In another embodiment, methods and agents are provided for enhancing the killing of tumors expressing immune privileged antigens by T lymphocytes. These methods include administering cytokines, inhibiting Fas-ligand expression in the tumor, and inducing the expression of MHC I molecules on the tumor. Other methods may be used in combination with increasing the immune-privileged T lymphocyte activity in the patient.

In a preferred embodiment, an individual with a tumor expressing an immune-privileged antigen and also suffering from a paraneoplastic disease or other syndrome in which the immune system is recognizing and attacking the same antigen at a non-tumor site within the body is treated by increasing the immune recognition of the immune-privileged antigen of the tumor exemplified by the non-limiting examples of methods disclosed herein, while concurrently protecting the non-tumor site from immune attack by the corresponding methods disclosed herein.

It is thus a principal object of the present invention to take advantage of the presence of immune-privileged antigen-specific T lymphocytes to detect the existence of a pathological state in a patient and to monitor the efficacy of treatments based upon the enhancement of tumor immunity by T lymphocytes as well as their suppression in the treatment of the associated syndrome in the non-tumor site. It is a further object of the present invention to provide both diagnostic and therapeutic purposes for the detection of tumors and paraneoplastic syndromes, to increase the immune destruction of such tumors as well as to protect the non-tumor organs susceptible to disease caused by the same T lymphocytes.

These and other aspects of the present invention will be better appreciated by reference to the following drawings and Detailed Description.

BRIEF DESCRIPTION OF THE DRAWINGS

FIG. 3 depicts cytofluorography of cells isolated from the CSF of a patient with acute PCD indicate a Th1-type cellular immune response. (A) Cells present in the CSF were assayed for various phenotypic markers by FACScan® (Becton Dickinson) using the indicated monoclonal antibodies; CD56 is a marker for natural killer cells; CD19 is specific for B cells; CD3 is present on all T cells; CD4 and CD8 indicate helper and cytotoxic T cell subsets, respectively; CD25 is the IL2 receptor and is a marker for activated T cells. A second analysis was performed after the patient received tacrolimus. * p<0.005. (B) Cells from the CSF were assayed for their intracellular cytokine profile using a dual laser fluorocytometer (Becton Dickinson). Cells were treated with brefeldin A (BFA), and stained for the presence of accumulated cytokines using the indicated monoclonal antibodies. T-blasts were selected based on forward scatter and these cells consisted of approximately 10% of the CD3+ CD4+ T cell population. (C) As a control, PBMCs were isolated at the same time and assayed as described in (B). In addition, the PBMCs were stimulated using phorbol 12-myristate 13-acetate and ionomycin allowing cytokine production to be detected as a positive control (23).

FIG. 7 shows the results of a simplified assay of cdr2-specific T cells present in the blood of a patient with PCD. Dendritic cells from a blood sample are matured, then exposed to apoptotic cells expressing cdr2. Subsequently, exposure of the cells to peripheral blood lymphocytes results in gamma-interferon production by T lymphocytes as an indicator of the number of cdr2-specific T cells in the individual.

DETAILED DESCRIPTION OF THE INVENTION

Figure 1:
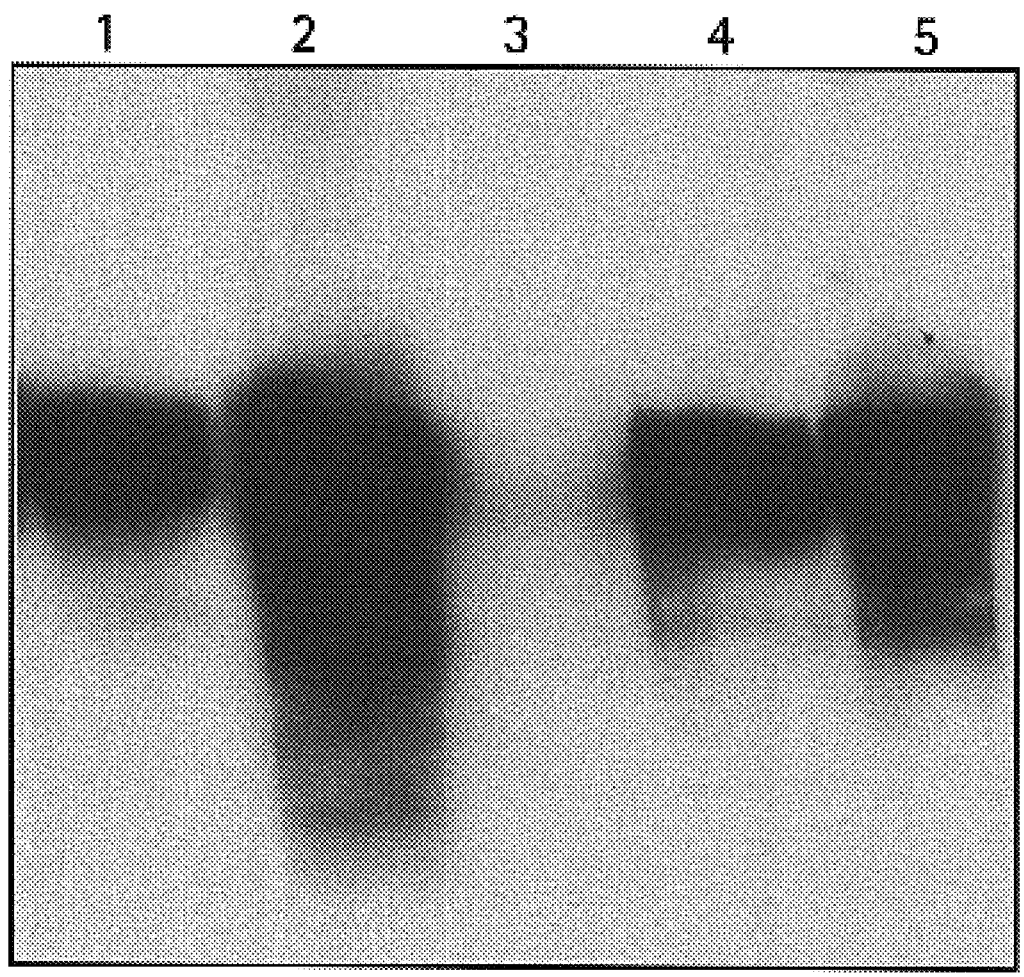
FIG. 1 depicts a Western blot analysis of patient's serum and CSF against the cloned cdr2 fusion protein (9). Serum (1:10,000 dilution) and CSF (1:500 dilution) from patient 1 (lanes 1, 4), patient 2 (lanes 2, 5), or serum from a patient with an irrelevant PND (Hu syndrome; 1:500 dilution; lane 3) was blotted. Serum and CSF from patient 3 gave similar results.

The terms "tumor," "cancer," "neoplasm," "neoplasia" and their etymological relatives are used interchangeably herein to refer generally to dysproliferative diseases and the attendant affected cells or cell masses. Preferably, the dysproliferative cells referred to herein express an immune-privileged antigen.

Cytotoxic T lymphocytes (CTLs) are effector T cells, usually CD8+, that can mediate the lysis of target cells bearing antigenic peptides associated with a MHC molecule. Other cytotoxic cells include γ/δ and CD4+ NK 1.1+ cells.

Immune privilege and immune-privileged antigen refer to the isolation of certain sites and antigens within the body from the immune system and thus relate to antigens to which an immune response is not normally developed. Immune-privileged antigens expressed ectopically (i.e., outside of their normally immune-privileged sites) may result in autoimmunity or tumor immunity. Immune-privileged antigens are expressed by some tumors resulting in an immune response to both the tumor and to non-tumor sites expressing the same immune-privileged antigens. Subsequent access of the immune effector cells to the immune privileged sites results in immune attack of non-tumor cells. One type of such immune-privileged antigens are neuronal antigens, a subset of which are the onconeural or paraneoplastic antigens, against which an immune response will cause neurologic disease. A more detailed description of the onconeural antigens may be found in reference (2), herein incorporated by reference.

Antigen presenting cells (APCs) are cells including dendritic cells, macrophages, and B cells, that can process and present antigenic peptides in association with class I or class II MHC molecules and deliver a co-stimulatory signal necessary for T cell activation.

It has been discovered by the inventors herein that the heretofore enigmatic etiology of the paraneoplastic syndromes, wherein individuals with a tumor experience disease at remote locations within the body leading to severe neurological impairment, is explained by the existence of cytotoxic T lymphocytes (CTLs) and memory T lymphocytes targeted against tumor antigens which also recognize identical antigens expressed on neurons. Such immune-privileged antigens expressed by tumor cells induce a cellular immune response which in some cases provides effective and desirable tumor immunity, but as an undesirable side effect mediates immune attack on normal tissues in immune privileged sites which also express the same antigen. Less well understood is access of CTLs to the immune privileged sites as well as the expression of the normally cytoplasmic immune-privileged antigens on non-tumor cells. As mentioned above, patients often experience the remote, adverse effects before detection of the tumor. Because the antigens recognized by specific CTLs are located in immune privileged sites within the body, for example, in the brain in paraneoplastic neuronal degeneration, the discovery herein provides an explanation for the poorly understood phenomenon of immune system attack on immune privileged, non-tumor antigens. In addition to the brain, other immune privileged sites in the body include the testis and parts of the eye.

In accordance with the present invention and as will be elucidated in the examples and description below, both diagnostic and therapeutic utilities are provided in which the presence or activity of T lymphocytes specific for immune-privileged antigens are usefully employed. Detection of T lymphocytes specific for immune-privileged antigens provides an opportunity for screening patients for the early detection of tumors which express such antigens, and facilitates the monitoring of patients undergoing anti-cancer therapies. Effective tumor immunity by such T lymphocytes may eradicate the tumor at an early stage but leave behind a paraneoplastic syndrome or autoimmune disease; detection of the cellular immune response and identification of the particular antigen to which it is directed may allow therapeutic intervention before the development of the neurological disease and may facilitate treatment of the persisting condition.

New methods of treatment of neoplasms as well as of paraneoplastic syndromes and autoimmune diseases is also provided by the appreciation of the role of T lymphocytes in the pathophysiology of the paraneoplastic syndromes and immunologic recognition of privileged antigens in general. The effectiveness of tumor immunity mediated by specific CTLs which recognize the immune-privileged antigen expressed by tumors is stimulated or enhanced by creating or expanding the population of specific CTLs or memory T lymphocytes. APCs exposed to the immune-privileged antigen are employed to enhance the immune response. Methods for the protection of non-tumor cells from immune attack are also provided, in order to protect the non-tumor target sites from pathology, especially when an immune response against the tumor is enhanced.

Among the various paraneoplastic syndromes, paraneoplastic cerebellar degeneration (PCD) is associated with gynecological tumors such as those of the ovary and breast. As will be seen in the examples below, CTLs present in PCD patients specifically lyse target cells presenting peptides derived from the PCD antigen called cdr2. Thus, cdr2 antigen, normally an immune-privileged antigen of neuronal cells, is expressed in gynecological tumors, enabling the induction of a cellular immune response to the antigen. T lymphocytes assayed directly from the serum of an acute PCD patient, as well as dendritic cell-stimulated memory T cells present in patients with chronic PCD, demonstrated cdr2-specific cytotoxicity.

The PCD antigen has been identified as cdr2, a protein expressed in neuronal cells and in gynecological tumors (9, 54). An investigation by the present inventors into the processing of the cdr2 antigen for presentation by APCs to T lymphocytes has led to the identification of polypeptide fragments of cdr2 which are targets for naturally-occurring CTLs in PCD patients. These peptides are believed to be those presented by dendritic cells in the development of cellular immunity. Eight peptides, namely cdr2-1 or Yo1 (SEQ ID NO:1), cdr2-2 or Yo2 (SEQ ID NO:2), cdr2-3 or Yo3 (SEQ ID NO:3), cdr2-4 or Yo4 (SEQ ID NO:4), cdr2-5 or Yo5 (SEQ ID NO:5), and cdr2-6 or Yo6 (SEQ ID NO:6), cdr2-7 or Yo7 (SEQ ID NO:7) and cdr2-8 or Yo8 (SEQ ID NO:8) have been synthetically prepared, and are used diagnostically and therapeutically in the practice of the present invention. Furthermore, and as will be described below in detail, engineering of cells to express these peptides has additional diagnostic and therapeutic utilities in the detection and treatment of cancer and paraneoplastic diseases.

In several other diseases, cellular immunity against antigens expressed by a tumor is responsible or presumed responsible for the attack of non-tumor cells expressing the same antigens. As described above, these syndromes may be subacute or acute, causing serious complications. Hu antigen is expressed by small cell lung tumors; Hu syndrome is another example of a neurological disease brought about by a cellular immune response to an immune-privileged antigen. The identification by the inventors herein of the role of cellular immunity in the etiology of these diseases provides the link between expression of non-tumor antigens at the affected site of the paraneoplastic syndrome and the expression of the antigen in the tumor.

As described above, the presence of cdr2-specific CTLs on a wide range of gynecological tumors suggests that breast or ovarian tumor cells expressing cdr2 are responsible for initiating PCD. However, the detection of cdr2 in a high percentage of non-PCD-associated tumors indicates that there are additional factors responsible for successful tumor immunity. Relevant factors include tumor cell expression of MHC-I (demonstrated in PND-associated tumors; ref 18) and the proximity of dendritic cells (DCs) to apoptotic tumors that may be necessary for cross-priming (19). It has been reported that 15% of patients with non-PND associated small cell lung cancer harbor low titers of the PND Hu antibody, and that this antibody response predicts limited tumor spread and a complete response to chemotherapy (5,20). The invention described herein is extended to the presence of Hu-specific CTLs in such patients. Similarly, it is expected that a significant percentage of patients with non-PND-associated gynecological tumors expressing cdr2 may be amenable to diagnosis and therapy by particular embodiments of this invention whereby the presence of cdr2-specific cytotoxic T lymphocytes are detected and their activity modulated in these patients. The present invention includes immune privileged antigens generally, not limited to those described herein in addition to Nova, β-NAP, etc.) and are taught to be relevant by this invention.

Thus, it is towards the detection and the modulation of the T lymphocyte response to immune privileged antigens that the present invention is directed. Enhancement of the immune response increases the effectiveness of antitumor activity. Suppression of the immune response alleviates the paraneoplastic or autoimmune disease. The diseases and syndromes that arise as a result of a cellular immune response to privileged antigens include, but are not limited to, paraneoplastic neuronal degeneration, paraneoplastic cerebellar degeneration, Hu syndrome, the Ri syndrome (opsoclonus-myoclonus ataxia associated with breast, fallopian tube and small cell lung cancer, and the Ri or Nova antigen), opsoclonus and myoclonus associated with neuroblastoma, vitiligo, myasthenia gravis, subacute motor neuropathy, subacute necrotic myelopathy, polyneuropathy, Eaton-Lambert syndrome, dermatomyositis and polymyositis. These conditions appear to be directly or indirectly related to neoplasia in the patient, either undetectable, overt, or as a result of a tumor which spontaneously regressed. In some cases, the identity of the antigen is not yet elucidated, but the course of the disease and its relationship with neoplasia and the other, better-studied diseases indicates a role for an as-yet identified immune-privileged antigen in the etiology of the disease. Furthermore, it is suspected that the above-mentioned diseases as well as various autoimmune disease may in fact arise from a cellular immune response to a neoplasm which was effectively eradicated by the immune response, but results in T lymphocytes attacking privileged antigen and evoking a syndrome far after the neoplasm is eradicated. The diagnostic and therapeutic methods of the present invention directed to the paraneoplastic diseases will also find utility in the diagnosis and therapy of the other immune-privileged antigen-related diseases, including autoimmune diseases.

In one embodiment of the present invention, quantitation of immune-privileged antigen-specific cytotoxic and memory T lymphocytes is performed in order to identify the presence and extent of a tumor or to confirm the diagnosis of a paraneoplastic or other syndrome, such as an autoimmune disorder, e.g. vitiligo. This test is performed as a routine assay such as a screening test or for individuals undergoing physical examination. It may also be performed in individuals suspected of having a neoplasm or a disease related to a cellular immune response to an immune-privileged antigen. In order to carry out the test, a sample of blood or other appropriate bodily fluid containing lymphocytes is obtained, such as cerebrospinal fluid (CSF).

In order to determine the presence of cytotoxic T lymphocytes that are specific for a particular immune-privileged antigen, any one of several types of assays is performed, all of which are known to one or ordinary skill in the art. By way of non-limiting examples, an assay is performed which identifies the presence of T lymphocyte receptors that recognize the immune-privileged antigen, i.e., peptide fragments of the antigen complexed in an HLA tetramer (51). In this assay, a specific antibody reagent is prepared that recognizes peptides of the immune-privileged antigen complexed with HLA; this reagent is used to detect T lymphocytes expressing the particular receptor. The reagent must be specific for the particular HLA haplotype of the patient. In a routine screening test, various combinations of immune-privileged antigens and HLA haplotypes is sought. Detection is achieved using any of a number of means, for example, with a fluorescent labeled reagent using fluorescence-activated cell sorting (FACS) techniques, or by using a detectable label such as a radioactive or enzymatic tag and quantitating the binding of the reagent to T lymphocytes in the sample by standard techniques. These various methods are provided by way of non-limiting examples to illustrate the practice of the invention, based upon the detection of CTLs that recognize immune-privileged antigens.

In another example of the means for detecting immune-privileged antigen-specific CTLs, the ability of such CTLs to lyse target cells expressing the immune-privileged antigen or a peptide thereof in the context of HLA is employed. Lysis of such cells by CTLs is detected by methods known to the skilled artisan. For preparation of the target cells expressing the appropriate HLA haplotype HLA-antigen peptide, any one of several methods is used. For example, the target cell may be one that expresses HLA, such as the cell line T2 (TAP$^{-/-}$ HLA-A2.1+), and will incorporate peptides into the HLA complex. The cells are pulsed with immune-privileged antigen peptides such as the cdr2 peptides described herein, and subsequently used as targets to detect specific CTLs. To detect specific recognition of the target cells by CTLs, lysis of the target cells is determined. For example, the target cells is preloaded with a marker such as Na$^{51}$CrO$_4$; lysis of the target cells results in the release of the label. Alternatively, lysis is assayed by the release of other intracellular markers such as intracellular enzymes, e.g., lactate dehydrogenase. These various methods are known to one of ordinary skill in the art. In a particular embodiment of the aforementioned method, the following steps are performed:

i) obtaining a sample of a bodily fluid;

ii) isolating T lymphocytes from the sample;

iii) preparing a sample of target cells bearing on the cell surface the immune-privileged antigen or a fragment thereof in the context of HLA;

iv) incubating the isolated T lymphocytes with the target cells;

v) quantitating the viability of the target cells; and iv) correlating the viability of said target cells with the presence of immune-privileged antigen-specific cytotoxic T lymphocytes in the sample.

In a further and preferred embodiment, the identification of CTLs specific for an immune-privileged antigen is readily determined by incubating T lymphocytes with the above-described target cells, and subsequently detecting the release of specific mediators from the CTLs indicative of the specific recognition and subsequent activation. CTLs encountering the antigen to which they are targeted are known to release γ-interferon and other cytokines including TNF-α, RANTES, MIP-1α and other chemokines, as well as to lyse target cells bearing the antigen. As an example of the practice of this preferred method, the following steps are carried out:

i) obtaining a sample of bodily fluid from an individual which contains T lymphocytes;

ii) optionally isolating T lymphocytes from the sample;

iii) exposing the body fluid sample or the isolated T lymphocytes to the immune-privileged antigen or fragment in the context of HLA;

iv) quantitating the level of a mediator produced by the T lymphocytes.

Cells expressing particular immune privileged antigens useful for the practice of these embodiment of the present invention include but is not limited to cells which naturally express immune privileged antigens, such as cdr2 expressed by HeLa cells; cells transfected with a gene which results in expression of the desired antigen, such as Drosophila cells; other examples are known to one of ordinary skill in the art. As described above, such transfected calls may additionally be engineered to express molecules of a particular HLA haplotype, and in addition may express co-stimulatory molecules. These cells may thus function as target cells which express the antigen in the context of HLA molecules, useful for the identification of immune-privileged antigen-specific T lymphocytes. A series of such cells may be prepared, each expressing a different HLA haplotype, for use in screening.

The level of γ-interferon or other mediators produced is directly related to the numbers of T lymphocytes specific for the immune-privileged antigen or fragment thereof present in the sample. This value is then used to identify a patient in which a tumor is or had been present, and the possibility of the development of a paraneoplastic syndrome or other disorder characterized by the presence of immune-privileged antigen-specific CTLs. Other methods for detecting antigen-specific CTLs are applicable to the practice of the present invention as adapted for measuring CTLs specific immune-privileged antigens. Examples provided to illustrate the invention are not intended to be limiting. For example, methods as described above to directly identify CTLs against immune-privileged antigens include detecting on the surface of T lymphocytes receptors capable of detecting tetramers comprising HLA molecule and immune-privileged antigen peptides. The selection of the immune-privileged antigen or its fragments for the assays of the present invention may be general or specific to the particular syndrome to be detected. For general screening, for example for cancer, a test comprises a mixture of the various known paraneoplastic antigens or fragments. After identifying a patient as having specific CTLs against a mixture of antigens, further screening is carried out to pinpoint the particular antigen. Such screening and further identification may then be used to direct the future course of therapy for the patient, for example, therapies to increase the CTLs against the particular tumor, and to reduce the severity of the paraneoplastic syndrome by suppressing the CTLs in non-tumor sites within the body; these therapeutic utilities are described in further detail below.

It has also been found by the inventors herein that memory T cells specific for the paraneoplastic antigen are present in individuals with paraneoplastic syndrome. In order to screen for or detect the presence and extent of memory T cells in a patient sample, suspected memory T cells must be exposed to APCs presenting the immune-privileged antigen. Detection of the resulting activated T lymphocytes is quantitated in a similar fashion to the detection of CTLs directly in a patient sample as described above. As a general example of the method, the assay is carried out by following steps:

I) obtaining a sample of bodily fluid containing T lymphocytes;

ii) optionally isolating T lymphocytes from the sample of bodily fluid;

iii) preparing differentiated APCs that have processed and are presenting the immune-privileged antigen;

iv) co-incubating the immune-privileged antigen-presenting APCs with the sample or the isolated T lymphocytes;

v) measuring immune-privileged antigen-specific T lymphocytes.

Measuring the immune-privileged antigen-specific T lymphocytes is accomplished by any one of a number of methods known in the art. For example, expression of receptors recognizing the HLA-peptide tetramer may be measured, or the extent of secretion of mediators from the T lymphocytes may be determined; alternatively, the cytolytic activity of the T lymphocytes towards target cells expressing the immune-privileged antigen in the context of HLA may be detected.

By way of non-limiting examples, the APCs may be dendritic cells, macrophages, B cells, microglial cells, fibrocytes, engineered cells containing MHC and secreting co-stimulatory molecules, among others. Various known methods are used to prepare the target cells expressing the desired peptide; for example, it may be achieved by delivering antigen through apoptotic cells which express the antigen or a peptide fragment, by use of heat shock proteins which direct proteins to the MHC, and the direct pulsing of the cells with protein or peptides. These examples are merely illustrative of examples of the practice of the present invention and are not intended to be limiting.

In the specific example wherein mediators such as γ-interferon production is used as the read-out of the assay, its level will be directly related to the numbers of memory T lymphocytes in the patient sample, and thus is correlated with the presence and extent of the neoplasm in said individual or the prior presence of a neoplasm. Cytolysis and quantitation of specific receptors also provides similar data.

In another aspect of the invention, an assay is provided for the detection of cdr2-specific T cells. This assay is rapid and offers the ability to screen large numbers of patient samples for the presence of cdr2-specific T cells in the form of a kit. The steps of this method are as follows:

i) obtaining a sample of blood;
ii) maturing dendritic cells in the blood sample;
iii) exposing the matured dendritic cells to apoptotic debris from unrelated cells expressing an immune-privileged antigen;
iv) co-incubating the immune-privileged antigen-exposed dendritic cells with the patient's peripheral blood lymphocytes; and
v) measuring interferon-γ released from the lymphocytes as a measure of stimulation.

The number of T cells stimulated by the immune privileged antigen-fed dendritic cells is an indication of the number of immune privileged antigen-specific T cells in the patient's peripheral blood. The apoptotic debris to which the dendritic cells are exposed may be, by way of non-limiting example, apoptotic, transfected cells expressing an immune privileged antigen such as cdr2. A negative control may be used in the assay, for example, the same cell line but not expressing the antigen.

As an example of the practice of the above procedure, peripheral blood is obtained from a patient and dendritic cells were matured as described in Example 1. These cells were then fed with apoptotic debris from unrelated (mouse) cells that do or do not express the cdr2 protein. Such cells expressing cdr2 protein may be prepared for example, as described in Example 6 below, such as PC7 or EC2 cells, by stably transfecting EL4 cells with pcDNA-cdr2, and determination of protein expression made by Western blot analysis. These fed DCs are then incubated with patient's peripheral blood lymphocytes, and interferon gamma (IFN-γ) release measured as an index of stimulation. Although IFN-γ release may be measured in any one of a number of ways, the standard ELISPOT assay provides a rapid method. For example, $10^5$ T cells are placed in a 96-well plate, previously coated with a monoclonal antibody specific for IFN-γ, and incubated with $10^4$-irradiated stimulator cells (such as EC2 or EL4). After 20 hours, the cells are washed out and IFN-γ spot forming cells (SFCs) are detected using a biotinylated anti-IFN-γ antibody, and an HRP-AEC (3-amino-9-ethyl-carbazole) staining procedure. SFCs reported per million cells.

In this example, nitrocellulose-bottom wells are plated with antibody to IFN-γ, release allowed to occur for 20 hours, plates are washed, and a second anti-IFN-γ antibody is added which was conjugated to biotin to allow calorimetric detection. The number of spots secreting IFN-γ directly correspond to the number of T cells in the assay that are stimulated by the DCs. By comparing the number of T cells stimulated by EL4-fed DCs (negative control) with the number stimulated by EC2-fed DCs, the number of cdr2-specific T cells in a patient's peripheral blood can be determined.

There are several advantages of this assay. First, there is no HLA restriction required as there is for CTL assays in which T2 (HLA A2.1) targets are killed, so that patients of any MHC haplotype can be assayed by this method. Second, the assay is relatively simple, can be performed from a peripheral blood draw, and can be performed by automated ELISPOT robots and readers. Third, although current methods allow DCs to be grown from a single 50 ml peripheral blood draw, this assay can ultimately be done without DCs as antigen presenting cells (APCs), using peripheral blood monocytes, which as a mixed cell population, have sufficient APCs to allow T cell stimulation.

Furthermore, the above-described assays are useful to determine whether a patient with a immune-privileged antigen-expressing tumor has a sufficient population of antigen-specific T lymphocytes to control the tumor or is a candidate for anti-cancer therapy, by quantitating T lymphocytes specific for the particular antigen. In addition, the method can be used for monitoring the effectiveness of therapies intended to modulate the population of antigen-specific T lymphocytes in a patient, i.e., increase the population for anti-cancer therapy, and decrease the population for protection of non-tumor sites and alleviation of for example the paraneoplastic syndrome, by measuring the numbers of cytotoxic and memory T lymphocytes in accordance with the methods described above. The assay readout can be compared to pre-established standards and ranges to enable the health care professional to direct the appropriate course of therapy based on assay results.

As a consequence of the discovery of the role of CTLs in paraneoplastic syndromes, the inventors herein have identified a further diagnostic modality to monitor the progression or predict the potential success of immune-privileged antigen CTL-based therapies as described hereinabove, and to determine the propensity for the development of the syndrome as a consequence of the participation of cytokines. Cytokines are known to promote the expression of cytoplasmic antigen via MHC-I molecules (21,22), and thus increased levels of cytokines may enhance the effectiveness of the killing of tumor cells by the therapeutic methods of the present invention. Conversely, cytokines present in pathological states, such as neoplasia or a paraneoplastic syndrome, can induce, accelerate or exacerbate the disease process by promoting the expression of antigens on non-tumor cells. This may also help explain the still poorly understood phenomenon of how immune-privileged antigen-specific CTLs which arise from the expression of the antigen on tumor cells, are able to first gain access to normally immune privileged body sites such as the central nervous system, perhaps through a cytokine-mediated weakening of the endothelium barrier, and secondly, to recognize and attack neuronal and other cells in which the antigen is normally cytoplasmic and not expressed on the surface. Measurement of cytokine levels in contact with the paraneoplastic syndrome-affected tissue is thus useful in assessing the severity or potential severity of the disease.

Diagnostic kits are embodied by the present invention which provide particular immune-privileged antigens or fragments for the use in detecting antigen-specific T lymphocytes in a sample of bodily fluid, in accordance with the various methods described above. For instance, immune-privileged antigen peptides, such as by way of non-limiting example, the several previously-described peptides of cdr2 predicted to bind to the binding domain of HLA, may be included in a kit for the preparation of target cells bearing antigenic peptides in the context of HLA. Another component of a kit comprises a labeled or tetrameric complex containing the HLA molecule and peptides, for direct detection of CTLs with receptors specific for the complex. Kit componentry will be specific to the type of assay to be performed and the type or types of immune privileged antigens to be detected.

As a result of the discovery by the inventors herein of the role of T lymphocytes in both the progression of paraneoplastic syndromes and in tumor immunity, several therapeutic modalities are provided that are directed to the enhancement of the immune response to the tumor, and the suppression of the immune response at the site of the affected non-tumor tissues. These therapeutic modalities are generally directed to either the enhancement or the diminution of the cellular immune response to privileged antigens, and has utility in the treatment of cancer, paraneoplastic syndromes and in other diseases in which an inappropriate immune response to immune-privileged antigens results in pathology, for example, autoimmune diseases. Depending on the patient's condition, the extent of application of either of these therapies may be appropriate; ideally, these may be applied simultaneously for optimizing the anti-cancer benefits of cellular immunity while protecting non-tumor cells from immune destruction. The effectiveness of these therapies disclosed as a consequence of the present invention is enhanced by concurrently providing other known means to increase the effectiveness of cellular immunity.

The therapeutic regimen of enhancing killing of tumor cells in a patient by increasing the number or activation state of immune privileged antigen-specific cytotoxic T cells in a patient is supported experimentally by the ability to develop an animal model wherein such cytotoxic T cells are elevated, yet the animal is not neurologically compromised. As will be shown in more detail in Example 5 below, this has been achieved using mice that were immunized using an apoptotic tumor cell, which results in the generation of potent cdr2-specific killer T cells. The apoptotic tumor cell was a cell line (PC7) generated by stably transfecting EL4 cells (a T cell lymphoma) with pcDNA-cdr2, and determination of protein expression made by Western blot analysis. Mice were immunized with irradiated PC7 cells, followed by harvesting the spleens of primed and naive littermates. Mixed lymphocyte/tumor cell cultures were established using MHC-matched target cells, EC2 cells, or TIB84 cells for purposes of restimulating primed T cells. After 5 days, responding T cells were collected and tested at various ratios in a standard chromium release assay. Alternatively, $CD8^+$ T cells were purified from the spleens of primed and naive mice using the MACS cell isolation system. Briefly, anti-CD8 antibody coupled to iron conjugated microbeads are incubated with splenocytes and CD8+ T cells are positively selected by passing the cells through a magnetic column. The positively selected $CD8^+$ T cells were used directly in an ELISPOT assay.

The results of the experiment showed specificity as demonstrated by the ability of T lymphocytes to lyse MHC-matched target cells expressing cdr2, EC2 cells, but not MHC-matched cells that lack cdr2 expression. As the PC7 cells are MHC-mismatched with respect to the C57/B6 mouse that was immunized, it is believed that this model system is analogous to the cross-priming of tumor cells evident in patients with PCD.

In addition to the killing assay, IFN-γ release was also demonstrated from T cells purified from PC7 immunized mice. This short term assay confirmed that high levels of CTL precursors exist in the immunized mice. As no immunized mice exhibited signs of neurologic dysfunction, these data indicate the ability to separate tumor immunity from the autoimmune neurodegeneration. As described above, cdr2-specific killer T cells have been identified in patients with effective tumor suppression and PCD. In addition, significant numbers of breast and ovarian tumors present in neurologically normal patients express the cdr2 target antigen. Therefore, the present study demonstrates in this model that stimulation of T cells able to kill cdr2-expressing tumor cells is possible without inducing autoimmune neurologic disease.

In a first embodiment, enhanced anti-tumor therapy is provided to a patient with a neoplasm expressing an immune-privileged antigen by increasing the number of immune-privileged antigen-specific cytotoxic T lymphocytes in the patient. The lymphocytes to be stimulated may either be the patient's own cells, stimulated in vivo or ex vivo, or they may be HLA-matched cells from another source, as will be described below. This increase can be effected by exposing APCs such as dendritic cells isolated from the patient ex vivo to one or more peptides of the particular antigen, or by other known means, whereby the antigen will be available for presentation to T lymphocytes. The antigen-exposed APCs are then reintroduced into the patient to stimulate the activation of specific T lymphocytes in vivo, or, the APCs, for example, dendritic cells, may be further exposed in vitro to T lymphocytes isolated from the patient, whereby presentation to T lymphocytes will induce the activation of antigen-specific CTLs. T lymphocytes or dendritic cells are reintroduced into the patient, wherein the CTLs will promote anti-tumor activity, and dendritic cells will stimulate additional CTLs in vivo. For example, to practice the first method, the following steps are followed:

i) isolating a quantity of dendritic cells from a sample of patient's blood;

ii) exposing the dendritic cells in vitro to the immune-privileged antigen fragment;

iii) reintroducing the antigen-exposed dendritic cells to the patient.

The aforementioned ex-vivo therapies may be achieved by any one of several, non-limiting methods, known to the skilled artisan. For example, memory T lymphocytes may be activated ex vivo by exposure to dendritic cells presenting the desired immune privileged antigen. In another non-limiting example, immune-privileged antigen-specific T lymphocytes may be isolated using the HLA-peptide tetramer as described above, and then expanded with cytokines, e.g., IL-2, or in the presence of dendritic cells, before reintroduction to the patient. Bulk T cells isolated from the patient may be exposed to dendritic cells presenting the antigen; then the activated, antigen-specific cytotoxic T lymphocytes may then be reintroduced to the patient.

As mentioned above, these methods may be enhanced by concurrent therapies which increase the effectiveness of T lymphocyte killing. Non-limiting examples include increasing cytokine levels, inhibiting the expression of Fas-ligand expression (44) on tumor cells to block apoptosis, inducing the expression of MHC I molecules on the tumor using, for example, Nef inhibitor or Nef-like protein(41), radiation therapy, tumor chemotherapy, Bax induction in the tumor (52) and inducing apoptosis of tumor cells using FLIP inhibitors (49).

In a further embodiment of the above example, to achieve an object of the present invention in enhancing cellular immune-based therapy to cancer patients in those at risk for the development of, or exhibiting, a PND, the above-described T lymphocytes and/or dendritic cells may be engineered to be sensitive to a drug such as gancyclovir by methods known to the skilled artisan (53). After introduction of the immune cells to the patient, any induction or exacerbation of a PND may be controlled by suppressing the introduced immune cell population by administration of the drug to which the cells are sensitive.

In the practice of the above method, certain immune-privileged antigens may not be adequately taken up by dendritic cells for presentation on the cell surface, nor will exposure of the dendritic cells to the intact antigen or its peptides allow for processing and presentation. In a further embodiment, the antigen is provided in a form which can be readily processed and presented. Among various known means for increasing antigen presentation by poorly immunogenic or poorly processed antigens, use of apoptotic cells expressing the desired antigen to deliver antigen to dendritic cells (17), in addition to other known means such as the use of viral vectors, naked and plasmid DNA, RNA, liposomes with nucleic acid to thereby transfect dendritic cells (50) have been described. In a preferred embodiment, delivery is achieved using cells which already express the desired antigen; for example, HeLa cells, which are useful in the above-described methods for the treatment of PND because they express the cdr2 antigen. These immune-privileged antigen-expressing cells are induced to become apoptotic before exposure to the APCs.

In another embodiment of the invention, a method of treatment of a patient with a paraneoplastic syndrome or other inappropriate cellular immune response to an immune privileged antigen is provided wherein suppression of cellular immunity is desired to intervene in the attack of non-tumor cells by antigen-specific CTLs. Such methods of treatment are targeted at decreasing or suppressing the cellular immune response against the specific immune-privileged antigen. Agents useful for this method of treatment include, but are not limited to, immunosuppressive agents such as tacrolimus, cyclosporin, corticosteroids, and azathioprine, which have been shown to eliminate CTLs. These agents are useful for the treatment of paraneoplastic syndromes as described herein, whereby CTLs targeted against immune-privileged antigens are eliminated. In a further embodiment, suppression of the attack of CTLs on immune privileged sites such as the brain is achieved by sealing the blood-brain barrier. This may be accomplished by the use of various agents known in the art, for example, corticosteroids. Protection of the brain to maintain immune privilege also may be achieved by upregulating Fas ligand expression (40).

Administration of an agent to suppress the cellular immune response against an immune-privileged antigen is directed to the body in general or to specific locations for increased effectiveness, for example, in the case of paraneoplastic syndromes, to the central nervous system, by intracranial or intrathecal administration. Such agents may be administered by parenteral injection, or for oral, pulmonary, nasal or other forms of administration. Appropriate dosage levels for treatment of the various conditions in various patients will be ascertainable by the ordinary skilled worker, considering the therapeutic context, age and general health of the recipient.

As a consequence of the discovery of the role of CTLs in paraneoplastic syndromes, the inventors herein have identified a further therapeutic modality to intervene in the development or progression of the syndrome by limiting the expression of the immune-privileged antigen by non-tumor cells. This is achieved by reducing the level of cytokines in contact with the non-tumor cells, as it is known that cytokines will promote the expression of endogenous antigen via MHC-I molecules (21,22). Treatment with inhibitors of cytokine production, such as corticosteroids, or anti-cytokine agents such as anti-cytokine antibodies, are provided as non-limiting examples. In the example of PND wherein CTLs attack neuronal cells in the central nervous system, anti-cytokine therapy delivered to the CNS is provided by means such as intrathecal administration as described above.

In a further embodiment, a method is provided for decreasing the recognition of non-tumor cells expressing paraneoplastic antigens by paraneoplastic antigen-specific T lymphocytes by contacting non-tumor cells with an agent which interferes with the recognition of paraneoplastic antigen by lymphocytes. Such agents include those which suppress the expression of MHC, and other agents which suppress antigen presentation, such as those which may switch a Th1 response to a Th2 response.

In a still further embodiment, means to decrease the sensitivity of non-tumor cells to CTLs are known and may be used in conjunction with the methods and agents of the present invention. By way of non-limiting examples; perforin-mediated CTL killing may be inhibited (43); apoptosis may be inhibited for example, by inhibitors of FLIP (39); reducing Bax expression in neurons (45); cytokines that promote the immune-privileged state may be administered, such as IL-10 and TGF-$\beta$ (46); and MHC I expression may be decreased (41).

As mentioned above, an optimal treatment regimen for a patient in need of a cellular immune-based anti-cancer therapy provides both the enhancement of the anti-cancer therapy and protects the non-tumor tissues and cells from the therapy. Thus, treatment to stimulate or expand the CTL population while protecting the non-tumor cells from attack by the CTLs is desirable. Since CTLs normally pass very minimally into the CSF, no additional therapeutic intervention may be needed; if additional measures are desirable, this can be achieved, for example, by administering to the patient an anti-cytokine agent as described above prior to the introduction of CTLs, or limiting the effective period of CTL therapy by providing a population of CTLs which may be specifically inactivated as described above. By way of non-limiting examples, immortalized, immune-privileged antigen-specific CTLs can be prepared from an immortalized cell line of the same HLA type as the patient. The antigen-specific CTLs can be expanded in vitro and introduced into the patient. In order to control the population of these cells within the patient and to avert the potential attack by these cells of non-tumor cells, the cells can be engineered to be sensitive to a certain drug, such as gancyclovir (53). In patients with tumors who otherwise are neurologically normal, such control may be unnecessary. Alternatively, in an example of an course of therapy using such cells for a patient with an existing PND, the patient can be first treated with an anti-cytokine agent and a blood brain sealing agent to reduce expression of the privileged antigen on non-tumor cells and to restrict access of the CTLs to the brain, respectively. Other means for protecting the brain include increasing FAS ligand expression in the brain (40), decreasing Bax expression in neurons (45), and decreasing cytokine levels in the brain (46). A gancyclovir-sensitive (53), immune-privileged antigen-specific, immortalized CTL line may then be introduced, and allowed to attack the tumor. The patient is closely monitored for the appearance of or the exacerbation of the paraneoplastic syndrome, which, if it begins to occur, the patient is administered gancyclovir to suppress the therapy partially or completely. This cycle may be repeated as necessary the effect the destruction of the neoplasm. As it is expected that most immune-privileged tumor patients do not have PND, this method is preferred in monitoring such patients.

As described above, the inventors herein have identified certain peptide fragments of paraneoplastic antigens, such as the cdr2-1 (SEQ ID NO:1) and cdr2-2 (SEQ ID NO:2) fragments of cdr2, which are believed to be the natively processed cdr2 peptides to which CTLs are targeted. As such, these peptides have utility in the diagnostic methods provided herein for identifying antigen-specific T lymphocytes, as well as therapeutic utilities in producing dendritic cells and other APCs presenting specific peptides.

Based on the above-described therapeutic utilities of the present invention, additional embodiments comprise kits for carrying out one or more of the therapeutic modalities described herein. In one embodiment, a kit for stimulating the production of T lymphocytes specific for immune privileged antigens comprises cells which express an immune-privileged antigen as well as MHC molecules which match that of the patient to be treated; the cells may further express co-stimulatory molecules. These cells may be derived from a cell line, such as a Drosophila cell line. The cells may be used for the in-vivo or ex-vivo stimulation of T lymphocytes. The kit may further comprise T lymphocytes from donors with the same HLA haplotype as the patient, in order to participate in the further stimulation of a cellular immune response to a tumor.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

General Methods

Peripheral blood was obtained from HLA A2.1+ PCD patients and normal donors in heparinized syringes or by leukapheresis. PBMCs were isolated using Ficoll-Hypaque (Pharmacia Biotech). T cell enriched (ER+) and T cell depleted (ER−) populations were prepared by rosetting with neuraminidase-treated sheep red blood cells as previously described (14). T cells were further purified from ER+ cells for the CTL recall assays by removing monocytes, natural killer (NK) cells, and B cells as described (14). DCs were generated from peripheral blood precursors by culturing ER− cells for 7 days in the presence of GM-CSF (Immunex Corp.) and IL-4 (Schering-Plough Corp.), followed by 4 days in monocyte conditioned medium (15).

Activated CTLs were detected using T-cells as effector cells in a conventional $Na^{51}CrO_4$ release assay directly after purification. T2 cells (a TAP−/−, HLA-A2.1+, class II− cell line) were pulsed for 1 hr with 1 mM of various peptides, loaded with $Na^{51}CrO_4$ and used as targets (14). Alternatively, memory CTL responses were stimulated using DCs pulsed for 4 hours with 1 mM of various peptides. After 7 days, responding T cells were assayed for cytolytic activity. Again, T2 cells pulsed with peptide served as targets. Specific lysis was determined by subtracting the percent cytotoxicity of unpulsed T2 cells (0–3%). PCD peptides, designated cdr2-1 (KLVPDSLYV) (SEQ ID NO:1) and cdr2-2 (SLLEEMFLT) (SEQ ID NO:2), were predicted based on anchor residues for HLA A2.1 and synthesized (Biosysnthesis Inc). Six other peptides derived from cdr2 were tested (data not shown). The control for these experiments included the use of the immunodominant influenza matrix peptide, GILGFVFTL (SEQ ID NO:9)

Monoclonal antibodies (MoAbs) to the following antigens were used: CD19, CD56, CD3, CD4, CD8, αβTCR, CD25, IFNγ, TNFα, IL2, IL4, CD14, HLA-DR (Becton Dickinson); CD83(Coulter Corp.). Cell populations from the peripheral blood and spinal fluid were phenotyped with a panel of MoAbs listed above and analyzed on a FACScan (Becton Dickinson). Additionally, the DCs prepared from the patients were assayed for phenotypic markers (CD14−CD83+HLA-DR+). Dead cells and contaminating red blood cells were excluded by forward and side scatter properties. Intracellular cytokine profiles were assessed using a dual laser fluorocytometer (Becton Dickinson). Cells were treated with BFA, an inhibitor of secretion, followed by cell fixation and permeabilization, and then intracytoplasmic staining of accumulated cytokines (23). As a control, PBMCs were treated with BFA and cytokine production was stimulated using phorbol 12-myristate 13-acetate [PMA] and ionomycin [I] (23). T helper cells were delineated by a CD3+ CD4+ phenotype and levels of IFNγ, TNFα, IL2 and IL-4 were determined.

EXAMPLE 1

Figure 2A:
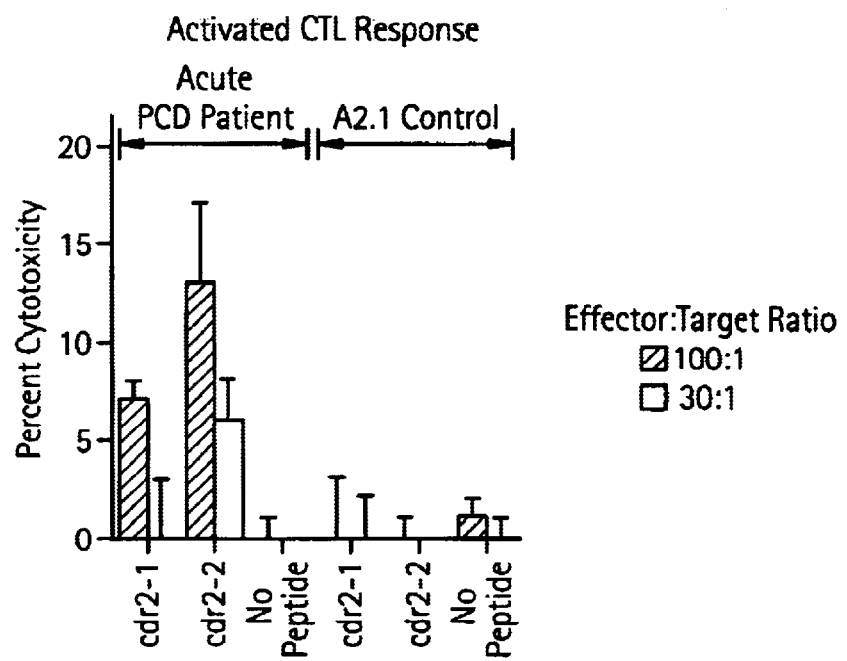
FIG. 2 demonstrates that Cdr2-specific killer cells are present in the peripheral blood of PCD patients. T lymphocytes were isolated from the peripheral blood of acute (A) and chronic (B) HLA-A2.1$^+$ PCD patients. (A) Isolated T lymphocytes were used directly in a chromium release assay using peptide pulsed T2 cells (a TAP$^{-/-}$HLA-A2.1$^+$ cell line) as targets. Peptides were predicted based on known anchor residues for the HLA-A2.1 binding groove, and designated cdr2-1 and cdr2-2. (B) Blood derived DCs were generated from PCD and HLA-A2.1$^+$ matched control individuals, pulsed with peptides and co-cultured with T cells. After seven days, the responding T cells were tested for cytolytic activity specific for cdr2 as determined by $^{51}$Cr release assay. The HLA-A2.1 immunodominant epitope derived from the influenza matrix protein served as a positive control for the generation of a CTL recall response (data not shown). Effector: target ratio=20:1. In (A) and (B), percent cytotoxicity is measured as a function of spontaneous and total release. Background killing of target cells was 0–3% in all groups. Results are representative of 6 experiments and the values shown represent the mean from triplicate wells.

Identification of cdr2-specific Cytotoxic and Memory T Lymphocytes in Patients with Paraneoplastic Cerebellar Degeneration Three PCD patients were studied to explore the nature of the immune response in the serum and spinal fluid. All patients had HLA-A2.1+ phenotypes. One (Patient 1) had acute disease and two (Patients 2 and 3) had chronic disease (seen 18 days, 9 months, and 6 months, respectively, after the onset of cerebellar dysfunction). The diagnosis of PCD was confirmed in each patient by demonstrating the presence of high titer cdr2 antibodies reactive with cloned fusion protein (FIG. 1), and peripheral blood lymphocytes were obtained for cellular immune assays. The possibility of that CD8+ CTLs are involved in tumor immunity in PCD was investigated using peptide-epitopes-derived from cdr2 in a standard chromium release assay. Target cells were T2 cells, a TAP$^{-/-}$ HLA-A2.1$^+$ cell line pulsed with cdr2 peptides (predicted for HLA-A2.1 based on determined anchor residues) and loaded with $Na^{51}CrO_4$. Effector T cells were obtained from peripheral blood (14) and incubated directly with targets at various effector:target ratios. In patient 1, cdr2-specific CTLs were detected showing specificity for the cdr2-2 and, to a lesser extent, cdr2-1 peptides (FIG. 2A). This response was titratable and specific for acute PCD, as no response was detected in an HLA-A2.1$^+$ normal control (FIG. 2A) or in either patient with chronic PCD (data not shown).

Figure 2B:
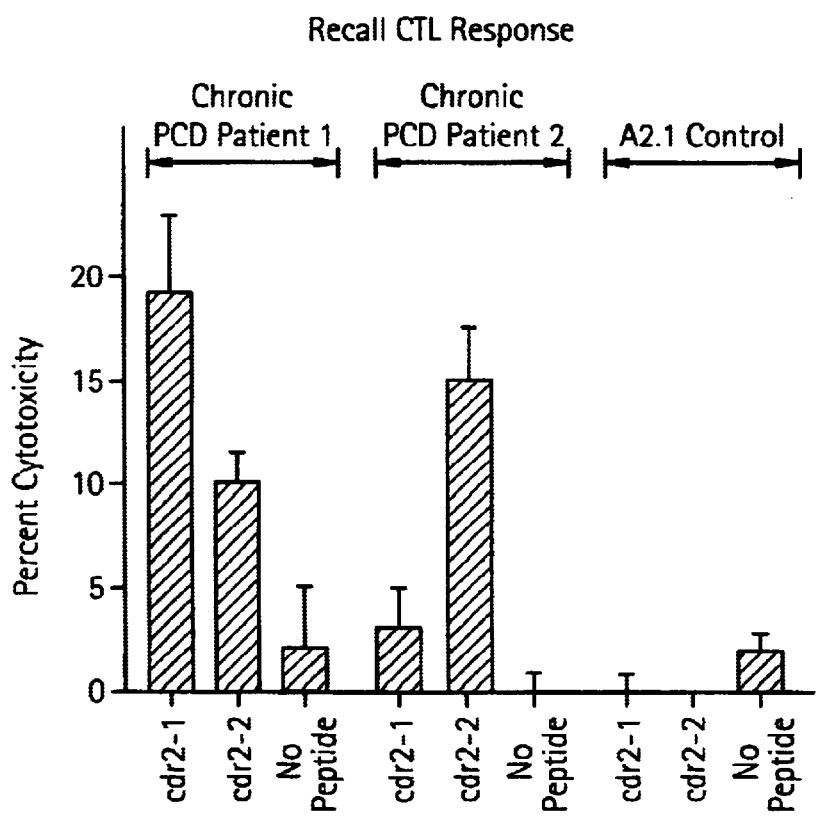

In order to examine whether memory T cells were present in the peripheral blood of PCD patients, an in vitro recall assay was established. Patients were leukaphereseed, providing a source of peripheral blood mononuclear cells (PBMCs). Terminally differentiated dendritic cells (DCs) were prepared by culturing a T cell depleted mononuclear fraction for 7 days in granulocyte-macrophage colony-stimulating factor (GM-CSF) and interleukin 4 (IL 4), followed by 4 days in monocyte conditioned medium (15). The DCs generated had a typical stellate morphology, were nonadherent, expressed characteristic maturation markers (i.e. CD83), and had potent T cell-stimulating capacity in mixed leukocyte reactions at stimulator to responder ratios of 300:1 or less (data not shown). These blood derived DCs were pulsed with eight different cdr2 peptides and co-cultured with purified syngeneic T cells (14). After 7 days, responding T cells were tested for cytolytic activity specific for cdr2 epitopes using peptide pulsed T2 cells as targets. In patients 2 and 3 (with chronic PCD), cdr2-specific CTLs were detected (FIG. 2B) using the cdr2-1 and cdr2-2 peptides. This CTL activity was not detected in 4 control individuals or in patient 1 (with acute PCD; FIG. 2B and data not shown). As a control for these experiments, CTL responses specific for the immunodominant HLA-A2.1 epitope derived from the influenza matrix protein were determined (data not shown).

EXAMPLE 2

Detection of Activated Cytotoxic T Lymphocytes in the Cerebrospinal Fluid of a Patient with Paraneoplastic Cerebellar Degeneration; Treatment with Tacrolimus Cerebrospinal fluid (CSF) analysis revealed that Patient 1 had a CSF pleiocytosis when first seen (99 WBC/mm$^3$). This enabled an evaluation of the autoimmune neurologic component of the patient's disorder by directly analyzing the CSF cells with cytofluorography and monoclonal antibodies specific for phenotypic cellular markers. Greater than 75% of the cells present were CD 3$^+$ $\alpha\beta$ T cells (FIG. 3A); approximately 40% of these were activated T blasts (CD25+ CD3+). Less than 5% of the cells were natural killer (NK) cells (CD56+), ~10% were B cells (CD 19+), and less than 2% of these cells were CD4$^-$/CD8$^-$ T cells (FIG. 3A). As a result of the acute nature of this patient's disease, some clinically evident residual cerebellar function, and the presence of activated T cells in her CSF (characterized by a CD25$^+$ CD3$^+$ phenotype), patient 1 was treated with tacrolimus (FK506), a drug which inhibits activation of T cells and partitions favorably into the CSF (16). The patient tolerated treatment for 10 days without side effects; however, evidence of recovery of cerebellar function was not observed. On day 11, treatment was discontinued and CSF was obtained for analysis, which revealed that the CD25$^+$ T cells had been eradicated (FIG. 3A). These results show that tacrolimus can effectively suppress activated T cells in the CSF of a PCD patient, and may be an effective alternative to treatments aimed at suppressing B cells or removing antibodies. Early intervention may be necessary to arrest clinical disease before there is excessive Purkinje cell death.

EXAMPLE 3

Intracellular Cytokine Staining of CSF Cells of Patient 1

To further define the activated cell population present in the CSF of patient 1, intracellular cytokine staining was performed and cells were assayed by four color cytofluorographic analysis. This revealed helper T cells present in the CSF which produced IL-2, IFN$\gamma$ and TNF$\alpha$ but not IL-4—a cytokine profile characteristic of Th1 cells (FIG. 3B). Furthermore, it was possible to demonstrate that the cells responsible for the production of these cytokines were activated T blasts (selected based on their increased forward scatter). In contrast, CD3$^+$ CD4$^+$ cells isolated from the peripheral blood of the same patient produced no cytokine unless stimulated with phorbol 12-myristate (PMA) and ionomycin (I) prior to analysis (FIG. 3B).

EXAMPLE 4

Demonstration of cdr2 Antigen on Gynecological Tumors

Figure 4A:
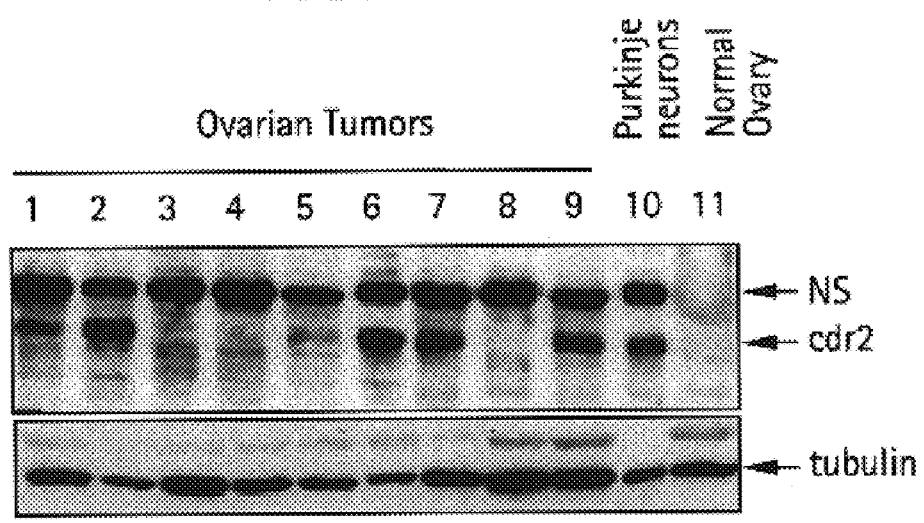
FIG. 4 shows a Western blot analysis of cdr2 expression in human ovarian tumors. (A) Protein extracts from 9 human ovarian tumors were run on Western blots and probed with biotinylated affinity purified PCD antibody. Strong cdr2 reactivity was evident in tumors 1, 2, 6, 7 and 9, as well as in extracts of human Purkinje neurons; there was no reactivity with a protein extract of normal human ovary. Probing a duplicate blot with an anti-tubulin antibody showed immunoreactive protein in each lane. A non-specific (NS) band was present in Purkinje extracts and ovarian tumors that reacted with avidin-horseradish peroxidase (HRP) secondary alone (data not shown). (B) IEF/SDS-PAGE analysis of cdr2 expression. An immunoreactive band of identical Mr and pI is present in extracts of mouse brain or a human ovarian tumor when probed with PCD antiserum and HRP conjugated secondary antibody. The mouse cdr2 cDNA encodes a protein that is 87% identical with human cdr2 (10), and this protein migrates identically with cdr2 detected in human Purkinje extracts (data not shown). Extraneous cross reactive bands seen in standard 1-D SDS gels (A) do not resolve on IEF.
Figure 4B:
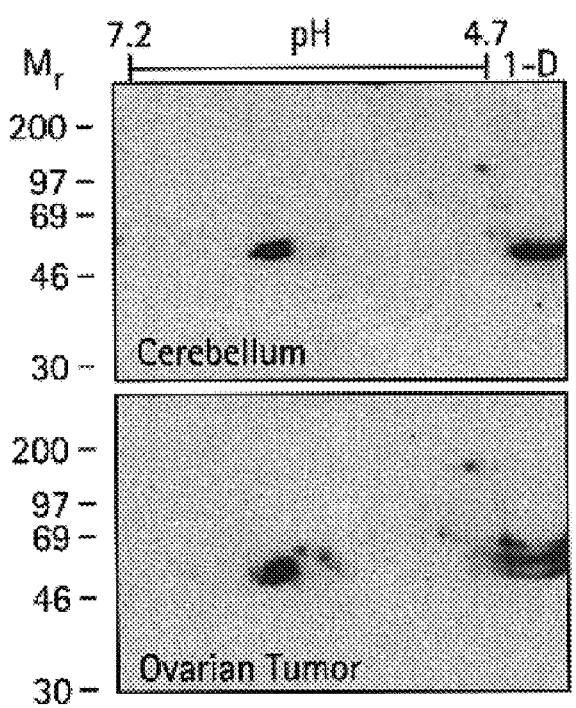
Figure 5:
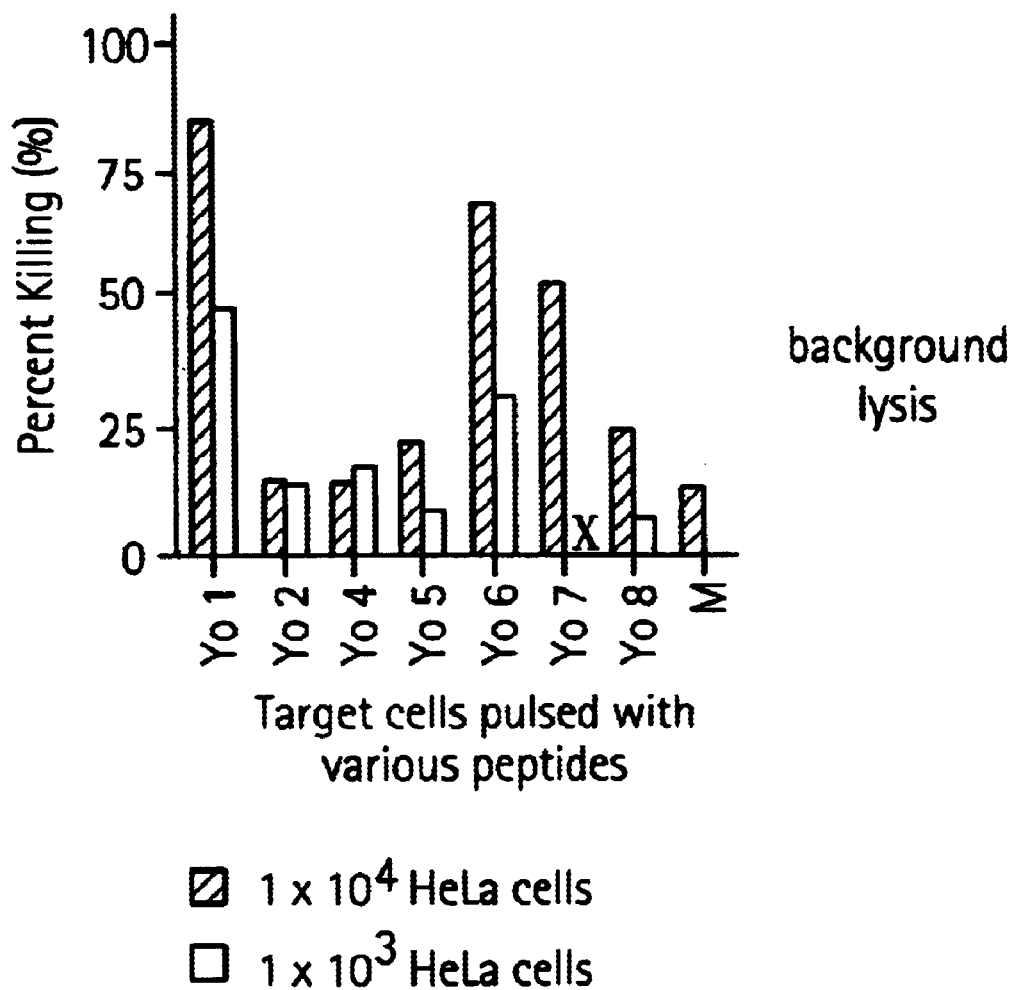
FIG. 5 shows that apoptotic cells expressing cdr2 may be used to present antigen to T lymphocytes. MC (97-09) DCs were co-cultured with apoptotic uninfected HeLa cells and syngeneic T cells. After 7 days, responding T cells were tested using T2 cells pulsed with various Yo peptides, Yo1 through Yo8 (corresponding to SEQ ID NO:1 through SEQ ID NO:8, and also referred to as cdr2-1 through cdr2-8). Negative control included testing Matrix peptide (M) (SEQ ID NO:9) pulsed T2 cells (HeLa cells were uninfected).

Despite the rarity of the paraneoplastic neurologic disorders, the target PND antigen in one such disorder (the Hu antigen) has been found to be expressed ubiquitously in its associated tumor type (small cell lung cancer). To evaluate whether the cdr2 antigen is present in a larger set of gynecologic tumors than the rarity of PCD might suggest, ovarian and breast tumor tissues obtained from neurologically normal individuals were examined for expression of cdr2 by Western blot analysis. Twelve of 19 tumors of ovarian epithelial cell origin expressed robust amounts of protein immunoreactive with PCD antisera (FIG. 4A and data not shown). To confirm that this antigen corresponded to the cdr2 antigen, the migration of immunoreactive antigen from cerebellum were compared with that from the tumor samples by 2D IEF/SDS-PAGE (FIG. 4B). These experiments confirm that the immunoreactive cdr2 band co-migrates in brain and tumor tissues, and demonstrate that a high percentage of non-PCD ovarian tumors express the cdr2 tumor antigen. Similar results were found in samples of non-PCD associated breast tumors, where at least 25 percent of tumors express the cdr2 antigen.

EXAMPLE 5

Use of Apoptotic Cells to Deliver Immune-Privileged Antigen to Antigen-Presenting Cells MC (97-09) DCs were co-cultured with apoptotic uninfected HeLa cells and syngeneic T cells. After 7 days, responding T cells were tested using T2 cells pulsed with various Yo peptides, Yo1 through Yo8 (corresponding to SEQ ID NO:1 through SEQ ID NO:8, and also referred to as cdr2-1 through cdr2-8). Negative control included testing Matrix peptide (M) (SEQ ID NO:9) pulsed T2 cells (HeLa cells were uninfected). These results show that successful induction of a cytotoxic T lymphocyte response to certain cdr2 peptides may be achieved by the use of apoptotic cells delivering the target antigen.

EXAMPLE 6

Generation of a Mouse Model that Recapitulates Aspects of the Tumor Immunity in the Disorder in the Absence of Autoimmune Neurologic Disease A mouse model of PCD was generated that recapitulates aspects of the tumor immunity in the disorder in the absence of autoimmune neurologic disease. Mice were immunized using an apoptotic tumor cell, PC7, which results in the generation of potent cdr2-specific killer T cells. The following cell lines were used in evaluating the model. For example, EC2 cells were generated by stably transfecting EL4 cells with pcDNA-cdr2, and determination of protein expression made by Western blot analysis.

TABLE 1

| Cell Line | Mouse of Origin | MHC allele | Antigen expression | Description |
|---|---|---|---|---|
| PC7 | DBA/2 | H-2$^d$ | cdr2 | cdr2-transfected P815 cells |
| P815 | DBA/2 | H-2$^d$ | parental | Mastocytoma tumor line |
| EC2 | C57BL/6 | H-2$^b$ | cdr2 | cdr2-transfected EL4 cells |

TABLE 1-continued

| Cell Line | Mouse of Origin | MHC allele | Antigen expression | Description |
|---|---|---|---|---|
| TIB84 | Balb/c | H-$2^b$ | Minor H of DBA/2 parental | Fibroblast line from congenic strain |
| EL4 | C57BL/6 | H-$2^b$ | | T cell lymphoma |

C57BL/6 mice were imumunized with $10^7$-irradiated PC7 cells, subcutaneously, at one week intervals for a total of two injections. One to three weeks after the second injection, the spleens of primed and naive littermates were harvested. Mixed lymphocyte/tumor cell cultures were established using EC2 cells or TIB84 cells for purposes of restimulating primed T cells. After 5 days, responding T cells were collected and tested at various ratios in a standard chromium release assay. Target cells included EC2 and EL4, demonstrating the generation of cdr2-specific killer T cells (A) and TIB84 and EL4, demonstrating the generation of allo-reactive T cells capable of recognizing minor histocompatibility antigens in the context of self-MHC I (B). Average values of triplicates from experimental wells (E) are compared to average values of spontaneous (S) and total (T) release as follows: % cytotoxicity=((E−S)/(T−S)) ×100. Naive littermates were used as negative controls. Alternatively CD8$^+$ T cells were purified from the spleens of primed and naive mice using the MACS cell isolation system. Briefly, anti-CD8 antibody coupled to iron conjugated microbeads are incubated with splenocytes and CD8$^+$ T cells are positively selected by passing the cells through a magnetic column. The positively selected CD8$^+$ T cells were used directly in an ELISPOT assay. $10^5$ T cells were placed in a 96-well plate, previously coated with a monoclonal antibody specific for IFN−, and incubated with $10^4$-irradiated stimulator cells (EC2 or EL4). After 20 hours, the cells were washed out and IFN− spot forming cells (SFCs) were detected using a biotinylated anti-IFN− antibody, and an HRP-AEC (3-amino-9-ethyl-carbazole) staining procedure. SFCs reported per million cells. (C).

Figure 6A:
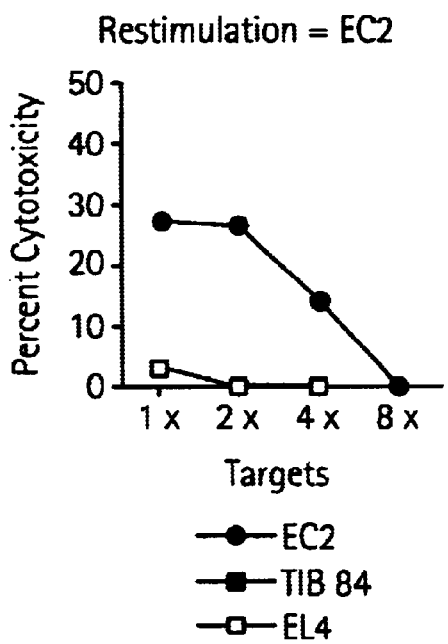
FIGS. 6 A–C show that apoptotic PC7 cells are capable of cross-priming cdr2-specific CD8+ T cells in vivo. Mice were immunized with apoptotic tumor cells which expresses cdr2, and potent cdr2-specific killer T cells were demonstrated, in the absence of any neurologic dysfunction.
Figure 6B:
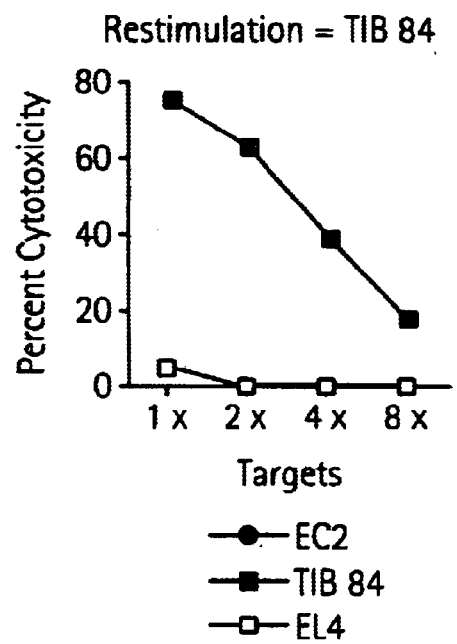
Figure 6C:
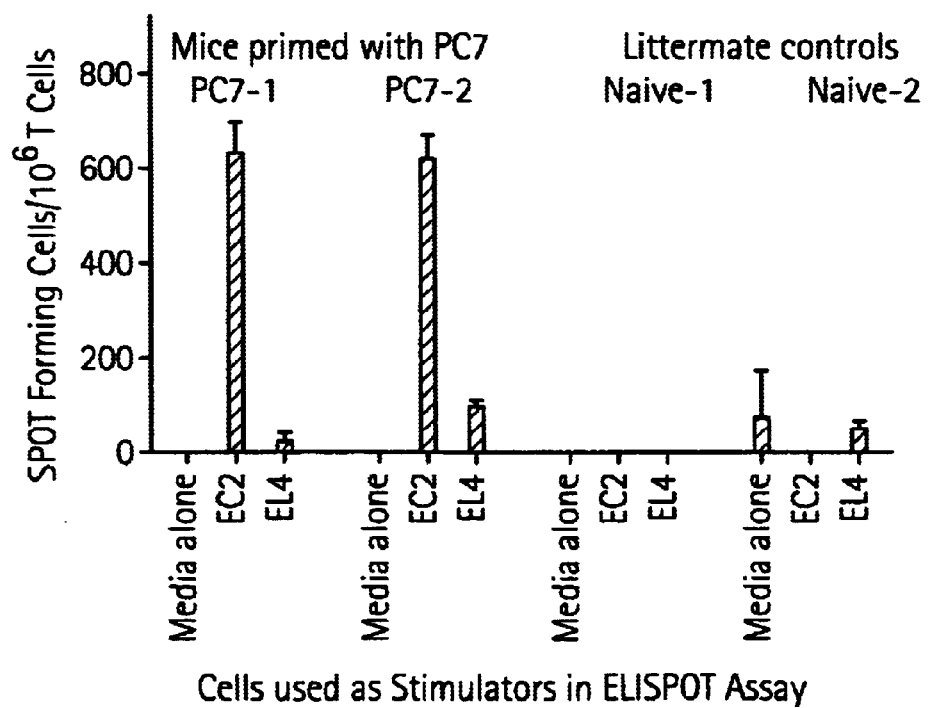

The results of the experiment are shown in FIG. 6. The specificity was demonstrated as measured by the ability to lyse MHC-matched target cells expressing cdr2, EC2 cells, but not MHC-matched cells that lack cdr2 expression, EL4 (FIG. 6A). As the PC7 cells are MHC-mismatched with respect to the C57/B6 mouse that was immunized, it is believed that this model system is analogous to the cross-priming of tumor cells evident in patients with PCD. A control for this experiment included the use of TIB84 cells as targets in the CTL assay (FIG. 6B), demonstrating the generation of allo-reactive T cells capable of recognizing minor histocompatibility antigens in the context of self-MHC I. As the PC7 cell also harbor allogeneic antigens with respect to the C57/B6 mouse, it was possible to stimulate allo-specific T cells that target the congenic line, TIB84. Congenic lines are useful as they contain allo-antigen presented in the context of self MHC molecules. Table 1 above provides the MHC haplotypes and cdr2 expression.

In addition to the killing assay, IFN-γ release was also demonstrated from T cells purified from PC7 immunized mice (FIG. 1C). This short term assay confirmed that high levels of CTL precursors exist in the immunized mice. No immunized mice exhibited signs of neurologic dysfunction. These data indicate the ability to separate tumor immunity from the autoimmune neurodegeneration. As described above, cdr2-specific killer T cells have been identified in patients with effective tumor suppression and PCD. In addition, significant numbers of breast and ovarian tumors present in neurologically normal patients express the cdr2 target antigen. Therefore, the present study demonstrates that stimulation of T cells able to kill cdr2-expressing tumor cells is possible without inducing autoimmune neurologic disease.

EXAMPLE 7

ELISPOT Assay for the Detection of cdr2-Specific T Cells

A new assay for the detection of cdr2-specific T cells was developed. This assay is faster and offers the ability to screen large numbers of patient samples for the presence of cdr2-specific T cells in the form of a kit. Peripheral blood was obtained from patients and dendritic cells were matured as described above. These cells were then fed with apoptotic debris from unrelated (mouse) cells that did not (EL4) or that did (EC2) express the cdr2 protein. EC2 cells were generated by stably transfecting EL4 cells with pcDNA-cdr2, and determination of protein expression made by Western blot analysis; please refer to Example 6 and Table 1 regarding these cells. These fed DCs were then incubated with patient's peripheral blood lymphocytes, and interferon gamma (IFN-γ) release measured as an index of stimulation. The assay for IFN-γ release is a standard ELISPOT assay. In this instance, the assay was done manually, by plating nitrocellulose-bottom wells with antibody to IFN-γ, allowing release to occur for 20 hours, washing plates, and adding a second anti-IFN-γ antibody which was conjugated to biotin to allow colorimetric detection. The number of spots secreting IFN-γ directly correspond to the number of T cells in the assay that were stimulated by the DCs. By comparing the number of T cells stimulated by EL4-fed DCs (negative control) with the number stimulated by EC2-fed DCs, the number of cdr2-specific T cells in a patient's peripheral blood can be determined.

In an example of the above method, DCs were grown from an HLA A2.1+ patient with PCD and ovarian cancer that was in remission. These cells were pulsed with either nothing, the HLA A2.1 immunodominant matrix peptide (MP) as a positive control, or apoptotic (irradiated) EL4 or EC2 cells. These DCs were then cultured together with T cells in varying ratios of T cell:apoptotic cell, as indicated. T cell activation was measured by counting spots corresponding to IFN-γ release as described. The results of the assay are shown in FIG. 7. This patient had a significant number of cdr2+ T cells evident by the large numbers of spots seen with EC2 stimulation, and the differences in spot number seen with EL4 versus EC2 fed cells. Negative controls included T cells incubated with apoptotic debris in the absence of DCs, and T cells incubated with neither DC nor apoptotic debris; neither control led to T cell stimulation.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

Various publications are cited herein, the disclosures of which are incorporated by reference in their entireties.

Literature Cited

1. T. Boon and L. J. Old, Curr Opin Immunol 9, 681 (1997).
2. Darnell, R. B. (1996). Onconeural antigens and the paraneoplastic neurologic disorders: at the intersection of cancer, immunity and the brain. Proc Natl Acad Sci USA 93: 4529–4536.
3. Dalmau, J., Graus, F., Rosenblum, M. K. & Posner, J. B. (1991). Anti-Hu associated paraneoplastic encephalomyelitis/sensory neuropathy: a clinical study of 71 patients. Medicine 71: 59–72.
4. Peterson, K., Rosenblum, M. K., Kotanides, H. & Posner, J. B. (1992). Paraneoplastic cerebellar degeneration. I. A clinical analysis of 55 anti-Yo antibody-positive patients. Neurology 42: 1931–1937.
5. Graus, F., Dalmau, J., Rene, R., Tora, M., Malats, N., Verschuuren, J. J., Cardenal, F., Vinolas, N., Garcia del Muro, J., Vadell, C., Mason, W. P., Rosell, R., Posner, J. B. & Real, F. X. (1997). Anti-Hu antibodies in patients with small-cell lung cancer: association with complete response to therapy and improved survival. J Clin Oncol 15: 2866–2872.
6. J. B. Posner and J. Dalmau, Curr Opin Immunol 9, 723 (1997).
7. Darnell, R. B. & DeAngelis, L. M. (1993). Regression of small-cell lung carcinoma in patients with paraneoplastic neuronal antibodies. Lancet 341: 21–22.
8. Devita, V. T., Hellman, S. & Rosenberg, S. (1989). Cancer, Principles and Practice of Oncology. In eds. (J. B. Lippincott Company, Philadelphia), pp. 1930–1931.
9. H. Fathallah-Shaykh, S. Wolf, E. Wong, J. Posner, H. Furneaux, Proc Natl Acad Sci USA 88, 3451 (1991). 10. J. P. Corradi, C. W. Yang, J. C. Darnell, J. Dalmau, R. B. Darnell, J Neurosci 17, 1406 (1997).
11. Smitt, P. A. E. S., Manley, G. T. & Posner, J. B. (1995). Immunization with the paraneoplastic encephalomyelitis antigen HuD does not cause neurologic disease in mice. Neurology 45: 1873–1878.
12. Sakai, K., Gofuku, M., Kitagawa, Y., Ogasawara, T. & Hirose, G. (1995). Induction of anti-Purkinje cell antibodies in vivo by immunizing with a recombinant 52-kDa paraneoplastic cerebellar degeneration-associated protein. J Neuroimmunol 60: 135–141.
13. M. Tanaka, K. Tanaka, O. Onodera, S. Tsuji, Clin Neurol Neurosurg 97, 97 (1995).
14. N. Bhardwaj et al., J Clin Invest 94, 797 (1994).
15. A. Bender, M. Sapp, G. Schuler, R. M. Steinman, N. Bhardwaj, J Immunol Methods 196, 121 (1996).
16. S. L. Schreiber and G. R. Crabtree, Immunol Today 13, 136 (1992).
17. M. L. Albert, B. Sauter, N. Bhardwaj, Nature 392, 86 (1998).
18. J. Dalmau et al., Cancer 75, 99 (1995).
19. G. Schuler and R. M. Steinman, J Exp Med 186, 1183 (1997).
20. Dalmau, J., Furneaux, H. M., Gralla, R. J., Kris, M. G. & Posner, J. B. (1990). Detection of the anti-Hu antibody in the serum of patients with small cell lung cancer—a quantitative Western blot analysis. Ann Neurol 27: 544–552.
21. Neumann, H., Cavalie, A., Jenne, D. E. & Wekerle, H. (1995). Induction of MHC class I genes in neurons. Science 269: 549–552.
22. Neumann, H., Schmidt, H., Cavalie, A., Jenne, D. & Wekerle, H. (1997). Major histocompatibility complex (MHC) class I gene expression in single neurons of the central nervous system: differential regulation by interferon (IFN)-gamma and tumor necrosis factor (TNF)-alpha. J Exp Med 185: 305–316.
23. L. J. Picker et al., Blood 86, 1408 (1995).
24. Posner, J. B. & Furneaux, H. M. (1990). Paraneoplastic syndromes. In Immunologic mechanisms in neurologic and psychiatric disease, Waksman, B. H., eds. (Raven Press, Ltd., New York), pp. 187–219.
25. Darnell, R. B. (1994). Paraneoplastic syndromes. In Current diagnosis in neurology, Feldmann, E., eds. (Mosby-Year Book, Inc., Philadelphia), pp. 137–141.
26. Anderson, N. E., Rosenblum, M. K. & Posner, J. B. (1988). Paraneoplastic cerebellar degeneration: clinical-immunological correlations. Ann Neurol 24: 559–567.
27. Hetzel, D., Stanhope, C., O'Neill, B. & Lennon, V. (1990). Gynecologic cancer in patients with subacute cerebellar degeneration predicted by anti-Purkinje cell antibodies and limited in metastatic volume. Mayo Clin Proc 65: 1558–1563.
28. Luque, F., Furneaux, H., Ferziger, R., Rosenblum, M., Wray, S., Schold, S., Glantz, M., Jaeckle, K., Biran, H., Lesser, M., Paulsen, W., River, M. & Posner, J. (1991). Anti-Ri: an antibody associated with paraneoplastic opso-clonus and breast cancer. Ann Neurol 29: 241–251.
29. Graus, F., Elkon, K. B., Cordon-Cardo, C. & Posner, J. B. (1986). Sensory neuronopathy and small cell lung cancer; antineuronal antibody that also reacts with the tumor. Am J Med 80: 45–52.
30. Lang, B., Newsom-Davis, J., Wray, D. & Vincent, A. (1981). Autoimmune aetiology for myasthenic (Eaton-Lambert) syndrome. Lancet ii: 224–226.
31. Patrick, J. & Lindstrom, J. (1973). Autoimmune response to acetylcholine receptor. Science 180: 821–822.
32. Furneaux, H. L., Reich, L. & Posner, J. P. (1990). Autoantibody synthesis in the central nervous system of patients with paraneoplastic syndromes. Neurology 40: 1085–1091.
33. Graus, F., Illa, I., Agusti, M., Ribalta, T., Cruz-Sanchez, F. & Juarez, C. (1991). Effect of intraventricular injection of an anti-Purkinje cell antibody (anti-Yo) in a guinea pig model. J Neurol Sci 106: 82–87.
34. Greenlee, J. E., Parks, T. N. & Jaeckle, K. A. (1993). Type IIa ('anti-Hu') antineuronal antibodies produce destruction of rat cerebellar granule neurons in vitro. Neurology 43: 2049–2054.
35. Graus, F., Vega, F., Delattre, J. Y., Bonaventura, I., Ren'e, R., Arbaiza, D. & Tolosa, E. (1992). Plasmapheresis and antineoplastic treatment in CNS paraneoplastic syndromes with antineuronal autoantibodies. Neurology 42: 536–40.
36. Lampson, L. (1987). Molecular bases of the immune response to neural antigens. Trends Neurosci 10: 211–216.
37. Medawar, P. (1948). Immunity to homologous grafted skin. III. The fate of skin homografts transplanted to the brain, to subcutaneous tissue, and to the anterior chamber of the eye. Br J Exp Pathol 29: 58–69.
38. Griffith, T. S., Brunner, T., Fletcher, S. M. Green, D. R. & Ferguson, T. A. (1995). Fas ligand-induced apoptosis as a mechanism of immune privilege. Science 270: 1189–1192.
39. Rensing-Ehl, A., Malipiero, U., Irmler, M., Tschopp, J., Constam, D. & Fontana, A. (1996). Neurons induced to express major histocompatibility complex class I antigen are killed via the perforin and not the Fas (APO-1/CD95) pathway. Eur J Immunol 26: 2271–4.

40. Saas, P., Walker, P. R., Hahne, M., Quiquerez, A. L., Schnuriger, V., Perrin, G., French, L., Van Meir, E. G., de Tribolet, N., Tschopp, J. & Dietrich, P. Y. (1997). Fas ligand expression by astrocytoma in vivo: maintaining immune privilege in the brain? J Clin Invest 99: 1173–8.
41. Collins, K. L., Chen, B. K., Kalams, S. A., Walker, B. D. & Baltimore, D. (1998). HIV-1 Nef protein protects infected primary cells against killing by cytotoxic T lymphocytes. Nature 391: 397–401.
42. Hammack, J., Kotanides, H., Rosenblum, M. K. & Posner, J. B. (1992). Paraneoplastic cerebellar degeneration. II. Clinical and immunologic findings in 21 patients with Hodgkin's disease. Neurology 42: 1938–1943.
43. Lowin, B., Hahne, M., Mattmann, C. & Tschopp, J. (1994). Cytolytic T-cell cytotoxicity is mediated through perforin and Fas lytic pathways. Nature 370: 650–2.
44. Hahne, M., Rimoldi, D., Schroter, M., Romero, P., Schreier, M., French, L. E., Schneider, P., Bornand, T., Fontana, A., Lienard, D., Cerottini, J. & Tschopp, J. (1996). Melanoma cell expression of Fas(Apo-1/CD95) ligand: implications for tumor immune escape [see comments]. Science 274: 1363–6.
45. White, F. A., Keller-Peck, C. R., Knudson, C. M., Korsmeyer, S. J. & Snider, W. D. (1998). Widespread elimination of naturally occurring neuronal death in Bax-deficient mice. J Neurosci 18: 1428–39.
46. D'Orazio, T. J. & Niederkorn, J. Y. (1998). A novel role for TGF-beta and IL-10 in the induction of immune privilege. J Immunol 160: 2089–98.
47. Tanaka, M., Tanaka, K., Idezuka, J., Tsuji, S. Failure to detect cytotoxic T cell activity against recombinant Yo protein using autologous dendritic cells as the target in a patient with paraneoplastic cerebellar degeneration and anti-Yo antibody. Exp. Neurol. 150:337 (1998).
48. Tollefson, A. E., Hermiston, T. W., Lichtenstein, D. L., Colle, C. F., Tripp, R. A., Dimitrov, T., Toth, K., Wells, C. E., Doherty, P. C. & Wold, W. S. (1998). Forced degradation of Fas inhibits apoptosis in adenovirus-infected cells. Nature 392:726–730.
49. Irmler, M., Thome, M., Hahne, M., Schneider, P., Hofmann, K., Steiner, V., Bodmer, J. L., Shroter, M., Burns, K., Mattmann, C., Rimoldi, D., French, L. E., and Tschopp, J. (1997). Inhibition of death receptor signals by cellular FLIP. Nature 388: 190–5.
50. Banchereau, J. and Steinman, R. M. (1998). Dendritic cells and the control of immunity. Nature 392:245–252.
51. Altman, J. D., Moss, P. A. H., Goulder. P. J. R., Barouch, D. H., McHeyzer-Williams, M. G., Bell, J. I., McMichael, A. J. and Davis, M. M. (1996). Phenotypic analysis of antigen-specific T lymphocytes. Scienct 274(5284) :94–96.
52. Sharma, K. and Srikant, C. B. (1998). Induction of wild-type p53, Bax, and acidic endonuclease during somatostatin-signaled apoptosis in MCF-7 human breast cancer cells. Int. J. Cancer 76:259–66.
53. Cohen, J. L., Boyer, O., Saloman, B., Onclercq, R., Charlotte, F., Bruel, S., Boisserie, G., & Klatzmann, D. (1997). Prevention of graft-versus-host disease in mice using a suicide gene expressed in T lymphocytes. Blood 89(12):4636–4645.
54. Sakai, K., Mitchell, D., Tsukamoto, T., & Steinman, L. (1990). Ann Neurol. 28:692–698.

---

What is claimed is:

1. A method for determining the presence and extent of a cellular immune response in an individual to an immune-privileged antigen, wherein the cellular immune response is associated directly or indirectly with a pathological state, the method comprising quantitating in a sample of bodily fluid from said individual the presence and extent of T lymphocytes specific for said immune-privileged antigen or fragments thereof, wherein the presence of T lymphocytes specific for the immune-privileged antigen or fragments thereof indicates the presence of a cellular immune response in the individual to an immune-privileged antigen.

2. The method of claim 1 wherein said pathological state is a dysproliferative disease, paraneoplastic syndrome, or an autoimmune disorder.

3. The method of claim 1 wherein said immune-privileged antigen is selected from the group consisting of paraneoplastic antigens, neuron-specific antigens, testis-specific antigens, and eye-specific antigens.

4. The method of claim 3 wherein said paraneoplastic antigen is an onconeural antigen.

5. The method of claim 4 wherein said onconeural antigen is selected from the group consisting of cdr2, Hu antigen, and Nova antigen.

6. The method of claim 1 wherein said T lymphocytes are cytotoxic T lymphocytes and said immune privileged antigen is an onconeural antigen.

7. The method of claim 6 wherein said onconeural antigen is cdr2.

8. The method of claim 1 wherein said T lymphocytes specific for said immune-privileged antigen are cytotoxic T cells and said method comprises detecting the extent of expression of T lymphocyte receptors capable of recognizing said antigen.

9. The method of claim 1 wherein said T lymphocytes specific for said immune-privileged antigen are cytotoxic T cells and said method comprises detecting the extent of activation of T lymphocytes upon exposure to said antigen.

10. The method of claim 1 wherein said T lymphocytes specific for said immune-privileged antigen are cytotoxic T cells and said method comprises detecting the extent of recognition by said cytotoxic T cells of target cells or target molecules expressing said antigen.

11. The method of claim 1, wherein said T lymphocytes specific for said immune-privileged antigen are cytotoxic T lymphocytes and said method comprises detecting the presence of T lymphocyte receptors that recognize the immune privileged antigen complexed with HLA.

12. The method of claim 1 wherein said T lymphocytes specific for said immune-privileged antigen are memory T cells and said method comprises detecting the extent of activation of said memory T cells after exposure to antigen presenting cells presenting said antigen.

13. The method of claim 1 wherein said T lymphocytes specific for said immune-privileged antigen are memory T cells and said method comprises detecting the extent of recognition of target cells expressing said antigen or a fragment thereof after exposure of said memory T lymphocytes to antigen presenting cells presenting said antigen.

14. The method of claim 13 wherein said fragment is selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

15. The method of claim 1 wherein said T lymphocytes specific for said immune-privileged antigen are memory T cells and said method comprises detecting the extent of recognition of target molecules bearing said antigen or a fragment thereof after exposure of said memory T lymphocytes to antigen presenting cells presenting said antigen.

16. The method of claim 15 wherein said fragment is selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

17. A method for screening individuals for the early onset or propensity to develop a pathological state caused by a cellular immune response to an immune-privileged antigen in accordance with claim 1.

18. A method for determining whether a neoplasm in an individual expresses an immune-privileged antigen by quantitating T lymphocytes from said individual that are specific for said antigen or a fragment thereof in accordance with claim 1.

19. The method of claim 18 wherein said fragment is a polypeptide sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

20. A method of determining whether a patient with a immune-privileged antigen-expressing tumor has a sufficient population of antigen-specific T lymphocytes to control the tumor or is a candidate for anti-cancer therapy by quantitating T lymphocytes specific for said antigen or fragment thereof in accordance with claim 1.

21. A method for monitoring the effectiveness of therapies directed to modulate the population of immune-privileged antigen-specific T lymphocytes in a patient by measuring the numbers of antigen-specific T lymphocytes in accordance with claim 1.

22. The method of claim 1 wherein said immune-privileged antigen is cdr2.

23. The method of claim 22 wherein the said fragment is selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

24. The method of claim 1 wherein said fragment is a polypeptide sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

* * * * *

UNITED STATES PATENT AND TRADEMARK OFFICE
CERTIFICATE OF CORRECTION

PATENT NO.     : 6,750,029 B1                                    Page 1 of 1
DATED          : June 15, 2004
INVENTOR(S)    : Robert B. Darnell, Matthew L. Albert and Nina Bhardwaj It is certified that error appears in the above-identified patent and that said Letters Patent is hereby corrected as shown below:

Title page,
Item [75], Inventors, change "Nina Bhardwai" to -- Nina Bhardwaj --

Signed and Sealed this

Twelfth Day of October, 2004

JON W. DUDAS
*Director of the United States Patent and Trademark Office*

SEQUENCE LISTING

<160> NUMBER OF SEQ ID NOS: 9

<210> SEQ ID NO 1
<211> LENGTH: 9
<212> TYPE: PRT
<213> ORGANISM: Homo sapiens

<400> SEQUENCE: 1

Lys Leu Val Pro Asp Ser Leu Tyr Val
 1               5

<210> SEQ ID NO 2
<211> LENGTH: 9
<212> TYPE: PRT
<213> ORGANISM: Homo sapiens

<400> SEQUENCE: 2

Ser Leu Leu Glu Glu Met Phe Leu Thr
 1               5

<210> SEQ ID NO 3
<211> LENGTH: 10
<212> TYPE: PRT
<213> ORGANISM: Homo sapiens

<400> SEQUENCE: 3

Gln Met Leu Gln Ser Glu His Pro Phe Val
 1               5                  10

<210> SEQ ID NO 4

-continued

```
<211> LENGTH: 10
<212> TYPE: PRT
<213> ORGANISM: Homo sapiens

<400> SEQUENCE: 4

Ser Leu Leu Glu Glu Met Phe Leu Thr Val
 1               5                  10

<210> SEQ ID NO 5
<211> LENGTH: 10
<212> TYPE: PRT
<213> ORGANISM: Homo sapiens

<400> SEQUENCE: 5

Thr Met Glu Glu Glu Tyr Gly Leu Val Leu
 1               5                  10

<210> SEQ ID NO 6
<211> LENGTH: 10
<212> TYPE: PRT
<213> ORGANISM: Homo sapiens

<400> SEQUENCE: 6

Glu Leu Glu Glu Thr Asn Gln Lys Leu Val
 1               5                  10

<210> SEQ ID NO 7
<211> LENGTH: 10
<212> TYPE: PRT
<213> ORGANISM: Homo sapiens

<400> SEQUENCE: 7

Ala Leu Lys Val Lys Tyr Glu Glu Leu Leu
 1               5                  10

<210> SEQ ID NO 8
<211> LENGTH: 10
<212> TYPE: PRT
<213> ORGANISM: Homo sapiens

<400> SEQUENCE: 8

His Leu Lys Lys Thr Val Thr Met Leu Gln
 1               5                  10

<210> SEQ ID NO 9
<211> LENGTH: 9
<212> TYPE: PRT
<213> ORGANISM: Homo sapiens

<400> SEQUENCE: 9

Gly Ile Leu Gly Phe Val Phe Thr Leu
 1               5
```